United States Patent
Shen et al.

(10) Patent No.: US 10,561,606 B2
(45) Date of Patent: *Feb. 18, 2020

(54) INJECTABLE LONG-ACTING LOCAL ANESTHETIC SEMI-SOLID GEL FORMULATIONS

(71) Applicant: Mira Pharma Corporation, Kenmore, WA (US)

(72) Inventors: Hui Rong Shen, Bothell, WA (US); Na Gan, Bothell, WA (US)

(73) Assignee: Mira Pharma Corporation, Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/212,206

(22) Filed: Dec. 6, 2018

(65) Prior Publication Data

US 2019/0167574 A1   Jun. 6, 2019

Related U.S. Application Data

(63) Continuation-in-part of application No. 15/833,899, filed on Dec. 6, 2017, now Pat. No. 10,220,093.

(51) Int. Cl.
| | |
|---|---|
| *A61K 9/24* | (2006.01) |
| *A61K 9/00* | (2006.01) |
| *A61K 9/06* | (2006.01) |
| *A61K 31/445* | (2006.01) |
| *A61P 25/04* | (2006.01) |
| *A61K 45/06* | (2006.01) |
| *A61K 47/14* | (2017.01) |
| *A61K 47/44* | (2017.01) |
| *A61K 31/573* | (2006.01) |

(52) U.S. Cl.
CPC ............. *A61K 9/0024* (2013.01); *A61K 9/06* (2013.01); *A61K 31/445* (2013.01); *A61K 31/573* (2013.01); *A61K 45/06* (2013.01); *A61K 47/14* (2013.01); *A61K 47/44* (2013.01); *A61P 25/04* (2018.01)

(58) Field of Classification Search
CPC .............................. A61K 47/14; A61K 9/0024
See application file for complete search history.

(56) References Cited

U.S. PATENT DOCUMENTS

| | | | |
|---|---|---|---|
| 4,079,038 A | 3/1978 | Choi et al. | |
| 4,093,709 A | 6/1978 | Choi et al. | |
| 4,131,648 A | 12/1978 | Choi et al. | |
| 4,138,344 A | 2/1979 | Choi et al. | |
| 4,180,646 A | 12/1979 | Choi et al. | |
| 4,304,767 A | 12/1981 | Heller et al. | |
| 4,946,931 A | 8/1990 | Heller et al. | |
| 5,700,485 A | 12/1997 | Berde et al. | |
| 6,214,387 B1 | 4/2001 | Berde et al. | |
| 6,521,259 B1 | 2/2003 | Chasin et al. | |
| 6,613,355 B2 | 9/2003 | Ng et al. | |
| 6,790,458 B2 | 9/2004 | Ng et al. | |
| 6,861,068 B2 | 3/2005 | Ng et al. | |
| 6,921,541 B2 | 7/2005 | Chasin et al. | |
| 7,053,209 B1 | 5/2006 | Gibson et al. | |
| 7,666,914 B2 * | 2/2010 | Richlin ................ | A61K 9/0014 424/428 |
| 8,182,835 B2 | 5/2012 | Kim et al. | |
| 8,221,778 B2 | 7/2012 | Siegel et al. | |
| 9,271,950 B2 | 3/2016 | Bannister et al. | |
| 10,220,093 B2 * | 3/2019 | Shen ..................... | A61K 47/14 |
| 2004/0001889 A1 | 1/2004 | Chen et al. | |
| 2005/0042194 A1 | 2/2005 | Ng et al. | |
| 2007/0184089 A1 | 8/2007 | Howie et al. | |
| 2014/0155485 A1 | 6/2014 | Bannister et al. | |
| 2015/0297729 A1 | 10/2015 | Ottoboni et al. | |
| 2015/0366967 A1 | 12/2015 | Shen et al. | |

FOREIGN PATENT DOCUMENTS

| | | |
|---|---|---|
| CN | 102458388 A | 5/2012 |
| CN | 102858374 A | 1/2013 |
| CN | 102869344 A | 1/2013 |
| CN | 102892408 A | 1/2013 |
| DE | 10033059 A1 | 1/2002 |
| JP | S62-045538 A | 9/1987 |
| JP | H07-508708 A | 9/1995 |
| JP | H08-143449 A | 6/1996 |
| JP | 2001-261558 A | 9/2001 |
| JP | 2004-501185 A | 1/2004 |
| JP | 2004-506697 A | 3/2004 |
| JP | 2007-521225 A | 8/2007 |
| JP | 2009-518374 A | 5/2009 |
| JP | 2010-522738 A | 7/2010 |
| KR | 10-2012-0046155 A | 5/2012 |
| WO | WO 1993/019736 A1 | 10/1993 |
| WO | WO 1997/044021 A1 | 11/1997 |
| WO | WO 2002/000203 A1 | 1/2002 |

(Continued)

OTHER PUBLICATIONS

Larsen et al. Journal of Controlled release, 2002, 81: 145-154.*
G Fetih, "Meloxicam formulations for transdermal delivery: hydrogels versus organogels", 2010, J. Drug Delivery Sci. Technol., 20(6), pp. 451-456.
Fernandez et al., "In Vitro Digestion of the Self-Emulsifying Lipid Excipient Labrasol.RTM. by Gastrointestinal Lipases and Influence of its Colloidal Structure on Lipolysis Rate", 2013, Pharmaceutical Research, vol. 30, Issue 12, pp. 3077-3087.
Yolles et al.; "Sustained Delivery of Drugs From Polymer/Drug Mixtures"; Polymer News; vol. 1; 1970; p. 9-15.
Packhaeuser et al.; "In situ forming parental drug delivery systems: an overview"; European Journal of Pharmaceutics and Biopharmaceutics; vol. 58 No. 2; 2004; p. 445-455.
International Patent Application No. PCT/US2015/050243; Int'l Search Report and the Written Opinion; dated Nov. 23, 2015; 13 pages.

(Continued)

*Primary Examiner* — Rei Tsang Shiao
(74) *Attorney, Agent, or Firm* — BakerHostetler

(57) ABSTRACT

What is disclosed is a controlled release pharmaceutical composition comprising a biocompatible and bioerodible semi-solid gel comprising a triglyceride of ricinoleic acid, a gelling agent, bupivacaine and, optionally, a corticosteroid, an analgesic, or an anti-inflammatory agent.

20 Claims, 5 Drawing Sheets

(56) References Cited

FOREIGN PATENT DOCUMENTS

| WO | WO 2002/015937 A2 | 2/2002 |
| --- | --- | --- |
| WO | WO 2007/066148 A1 | 6/2007 |
| WO | WO 2008/117268 A2 | 10/2008 |
| WO | WO 2010/142457 A1 | 12/2010 |
| WO | WO 2011/075623 A1 | 6/2011 |
| WO | WO 2011/121034 A2 | 10/2011 |
| WO | WO 2011/121082 A1 | 10/2011 |
| WO | WO2011121082 * | 10/2011 |
| WO | WO 2014/134586 A2 | 9/2014 |

OTHER PUBLICATIONS

International Patent Application No. PCT/US2015/050243; Int'l Preliminary Report on Patentability; dated Dec. 13, 2016; 21 pages.

Barr et al.; "Post Surgical Pain Management with Poly(ortho esters)"; Advanced Drug Delivery Reviews; Oct. 2002; vol. 54 Issue 7; p. 1041-1048.

Soderberg et al.; "In-vitro release of bupivacaine from injectable lipid formulations investigated by a single drop technique—relation to duration of action in-vivo"; Journal of Pharmacy and Pharmacology; vol. 54 No. 6; 2002; p. 747-755.

Griffin; J. So Cosmetic Chem.; 5:249-35; 1954.

Sokolsky-Papkov et al.; "Poly(DL:Lactic Acid-Castor Oil) 3:7-Bupivacaine Formulation: Reducing Burst Effect Prolongs Efficacy In Vivo"; Journal of Pharmaceutical Sciences; vol. 99 No. 6; Jun. 2010; p. 2732-2738.

Santamaria et al.; "Drug-Delivery systems for prolonged duration local anesthesia"; Materials Today; vol. 20 No. 1; Jan./Feb. 2017; p. 22-31.

Cremer Care; "Softigen 701"; http://www.petercremerna.com/products/657474081; accessed Sep. 26, 2017.

Sokolsky-Papkov et al.; "Prolonged Local Anesthetic Action Through Slow Release from Poly (Lactic Acid Castor Oil)"; 2009; Pharmaceutical Research; 26(1):32-39.

Larsen et al.; "Characteristics of drug substances in oily solutions. Drug release rate, partitioning and solubility"; 2002; International Journal of Pharmaceutics; 232: 107-117.

Zausig et al.; "Lipophilicity of local anesthetics and success of lip emulsion therapy"; 2012; Crit. Care Med; 40(1): 359-360.

Larsen et al.; "Assessment of Drug Release from Oil Depot Formulations Using an in Vitro Model-Potential Applicability in Accelerated Release Testing"; 2008; Drug Development and Industrial Pharmacy; 34:297-304.

Cognis, Nutrition & Health: Product Datasheet: Myrito® 318 PH; https://e-applications.basf-ag.de/data/basf-pcan/pds2/pds2-web.nsl/8C45C964E30F90BDC12573B100597C06/$File/MYRTOL_r_318_PH_E.pdf; accessed Oct. 16, 2016.

Juarez-Soberanez et al.; "Gelucire 39/01 as Excipient for Gastroretentive Metronidazole Sustained Delivery"; 2011; International Journal of Pharmacy and Pharmaceutical Sciences; vol. 3 (Supp 2): 86-91.

Graton et al.; "Hydrogen-Bond Accepting Properties of New Heteroaromatic Ring Chemical Motifs: A Theoretical Study"; Journal of Chemical Information and Modeling; vol. 56; 2016; p. 322-334.

Sokolsky-Papkov et al.; "Long-Acting Poly(DL:Lactic Acid-Castor Oil) 3:7-Bupivacaine Formulation: Effect of Hydrophobic Additives"; Pharm. Res.; vol. 28, 2011; p. 3265-3273.

Leslie Harris O'Hanlon; FDA declines approval of testosterone drug for third time; https://www.thelancet.com/journals/landia/article/PIIS2213-8587(13)70040-8/fulltext; The Lancet Diabetes & Endocrinology; vol. 1 Special Issue S14; Jun. 13, 2013; accessed Jan. 17, 2019; 6 pages.

Soderberg et al.; "The "inverted cup"—A novel in vitro release technique for drugs in lipid formulations"; Journal of Controlled Release; vol. 113; 2006; p. 80-88.

Larsen et al.; "In vivo release of bupivacaine from subcutaneously administered oily solution. Comparison with in vitro release"; Journal of Controlled Release; vol. 81; May 2002; p. 145-154.

International Patent Application No. PCT/US2018/064325; Int'l Search Report and the Written Opinion; dated Mar. 28, 2019; 17 pages.

* cited by examiner

INJECTABLE LONG-ACTING LOCAL ANESTHETIC SEMI-SOLID GEL FORMULATIONS

CROSS-REFERENCE TO RELATED APPLICATIONS

This application claims priority to U.S. application Ser. No. 15/833,899, filed Dec. 6, 2017.

TECHNICAL FIELD

What is described herein relates to a controlled release, semi-solid pharmaceutical composition comprising a local anesthetic and an anti-inflammatory drug in a semi-solid lipid vehicle comprising castor oil and a gelling agent, in the form of an injectable formulation for controlled delivery of the local anesthetic for treatment of post-operative pain.

BACKGROUND

Approximately 100 million surgeries are performed each year in the US and systemic opioids are used to manage postoperative pain, and pain is only adequately controlled in half of patients. Opioid postoperative pain management prescriptions are fueling the opioid epidemic as 1.6 million U.S. surgical outpatient become long-term opioid users each year with 10% of these becoming addicted to opioids. This dire scenario is a result of permissive opioid prescribing, and inadequate pain coverage particularly within the first 24 hours post-surgery. Moreover, only 38% of opioids prescribed at discharge are used leaving a huge reservoir of pills available for misuse and illicit diversion.

In an effort to reduce the need for opioid medications, anesthetics are administered locally, via an epidural injection, peripheral nerve block, or local infiltration. Unfortunately, the duration of action of presently approved anesthetics is less than 12 hours. The 24-hour period immediately following surgery is the most painful and requires robust analgesia coverage to ensure pain relief and opioid abstinence. As more outpatient surgeries are being performed, adequate pain control upon discharge is crucial.

A prolonged-release formulation of the approved anesthetic, bupivacaine encapsulated within liposomes (EXPAREL®) provides a longer duration of action compared to aqueous bupivacaine, pain relief is generally only for 24 hours with an associated slight reduction in opioid use.

In a Phase 2 bunionectomy study using HTX-011, a pharmaceutical formulation comprising an anti-inflammatory, meloxicam, and bupivacaine poly (ortho ester) to treat post-operative pain, 16% of patients remained opioid free post bunionectomy, compared to 7% of patients using aqueous bupivacaine alone. Viscusi, 2017, J Am Coll Surg, 225(Supp 2):e37.

Research effort has been made to synthesize hydrolysis-resistant polyester-poly(lactic acid-co-castor oil) for sustained release formulations of bupivacaine. Bupivacaine has been incorporated into hydrophobic, hydrolysis-resistant polyester-poly(lactic acid-co-castor oil) at 10% (w/v), resulting in a slower degradation rate, prolonged drug release, and 1-2 days of nerve block. Sokolsky-Papkov, 2009; Pharma Res, 3:7-10, and Sokolsky-Papkov; 2010, J Pharma Sci, 99: 2732-38. This fatty acid based biodegradable polymer released 60% of stored bupivacaine during one week without a burst of drug release. A single injection of the formulation caused motor blockade for 64 hours and sensory blockade for 96 hours. However, the formulation suffered significant burst release that led to systemic toxicity. Increasing the bupivacaine concentration to 15% (w/v) prolonged the duration of sensory blockade to 96 hours and exhibited less burst release than with 10% bupivacaine. This effect was attributed to increased formulation density and hydrophobicity, resulting in reduced water penetration into the drug-polymer matrix.

10% (w/v) bupivacaine in injectable and biodegradable poly(sebacic-co-ricinoleic acid) was shown to prolong sciatic nerve blockade from 8 to 30 hours. Shikanov, 2007, J Control Release 117:97-103. Incorporation of anhydride bonds (which undergo hydrolysis) in the polymer backbone rendered the formulation biodegradable. In vitro, 70% of the incorporated drug was released over the course of one week.

Much effort has been made to develop controlled release local anesthetic drug products. The drug delivery vehicle typically consists of a polymeric matrix from which drug is released by diffusion and/or degradation of the matrix. The local anesthetic is typically entrapped or encapsulated in microspheres or microparticles which can be administered into the surgical cavity by injection or infusion in the form of implant. Various publications describe release properties of local anesthetics from glyceride media, as follows.

Larsen, 2008; Drug Develop Indust Pharm, 34:297-304) discloses results of measuring rates of release of bupivacaine from various oils. Larsen discloses applying an in vitro measurement under nonsink conditions (rotating dialysis cell) to model drug release following intra-articular injection to a joint cavity. Larsen discloses rates of release of bupivacaine from fractionated coconut oil (a mixture of $C_8$ and $C_{10}$ saturated fatty acids) 80% release of the bupivacaine from the oil in less than two hours. Larsen also discloses results of measuring release of bupivacaine from MYRITOL® 318 PH (a triglyceride having a mixture of $C_8$ and $C_{10}$ saturated fatty acids) that were comparable to coconut oil. Larsen discloses that castor oil is considered the preferred excipient to modify drug release from oil solutions based on its history of parenteral administration. Larsen also discloses release rates of naproxen from a variety of oils, including MYRITOL® 318 PH, castor oil, SOFTIGEN® 701 alone or in combination with isopropyl myristate (IPM), and IMWITOR® 742 in combination with IPM, and that drug release rates from castor oil were slower than from other vegetable oils, most likely reflecting the hydrogen bond donating capability of the ricinoleic acid hydroxy group.

Castor oil has been used as a solvent in a commercial drug product AVEED® (testosterone undecanoate) injection for testosterone replacement therapy for intramuscular (gluteal muscle) administration. O'Hanlon, 2013, Lancet, special issue 1(S14) https://doi.org/10.1016/S2213-8587(13)70040-8. The U.S. Food and Drug Administration (FDA) found care must be taken to avoid intravascular injection because inadvertent escape of AVEED® into the vascular system may lead to vascular occlusion and short-term (60 minutes or less) consequences of pulmonary oil microembolism (POME) characterized primarily by cough, but sometimes with other associated symptoms. Id. The mechanical occlusion of the pulmonary vasculature from oil microembolization can cause acute transient pulmonary hypertension, resulting in a wide range of symptoms, from mild cough to circulatory collapse. It is postulated that POME results from microembolization of the oil drops to the lung vasculature, causing respiratory symptoms. Although other drug products also contain castor oil, the volume of castor oil in AVEED® is relatively greater than that of other products. Immediate/ rapid release/dump of high volume of castor oil by IM injection may lead to vascular occlusion and potential short-term/transient POME.

Sundberg WO 2011/121082 discloses an aqueous stabilized pharmaceutical gelling composition comprising (a) an anesthetically effective amount of one or more local anesthetics selected from bupivacaine or lidocaine; (b) a monoglyceride or diglyceride, or mixture thereof of a long chain fatty acid in an amount of between 15 to 70% by weight, and (c) a free long chain saturated or unsaturated fatty acid, and/or (d) one or more solubilizers consisting of polysorbates, sorbitan fatty acid ester, glycerol formal, or a polyoxyethylated castor oil, in an amount of between 0 to 30% by weight. These compositions are for topical administration supported by results of an in vitro mucoadhesion test.

Richlin U.S. Pat. No. 7,666,914 discloses a composition for locally delivering and localizing comprising a local anesthetic agent selected from bupivacaine or mepivacaine, and an anti-inflammatory agent selected from ketoprofen, meloxicam, and naproxen.

While the above systems are useful, their manufacture processes are complicated, cumbersome and expensive. In addition, they are often associated with an initial higher release of drug immediately after injection (also called "burst") followed by inconsistent and poor drug release kinetics, thus lack of reliability in pain relief in animal studies and human trials. There remains a need for controlled release of drugs suitable for pain management. Therefore, a more effective sustained release anesthetic is needed to effectively manage postsurgical pain with a rapid onset of action for coverage over the first crucial 24 hours and then prolonged duration through 72 hours.

SUMMARY

One aspect of the description is a pharmaceutical composition, comprising
(A) a glyceride mixture comprising
  (i) triglyceride of ricinoleic acid; and
  (ii) glycerides selected from the group consisting of (a) a mixture of triglyceride esters of $C_{12}$ to $C_{18}$ fatty acids, with a higher fraction of the long chain fatty acids (SUP DM) (b) a mixture of glycerides of $C_{12}$ to $C_{18}$ fatty acids (G43/01); (c) a mixtures of triglyceride, diglyceride or monoglyceride (WIT E85); and (d) a mixture of C10 to C18 fatty acid triglycerides (SUP D); or other solid glycerides with a melting point between 37° C. and 75° C.;
  wherein the ratio (i):(ii), is 10:1 to 6:3 (w:w); and
(B) active agents comprising (i) a therapeutically effective amount of bupivacaine to provide analgesia for at least two days; and, optionally, (ii) a corticosteroid, an analgesic or an anti-inflammatory agent;
  wherein the active agents are solubilized in the glyceride mixture at a concentration of 0.01-60 wt %; and wherein the pharmaceutical composition is a semi-solid gel which is biocompatible, bioerodible, homogeneous, and a single phase; and wherein the pharmaceutical composition consists of a semi-solid gel with a viscosity of 50-2000 cPs at 30° C.

In one embodiment of the pharmaceutical formulation, the active agents comprise a corticosteroid, an analgesic or an anti-inflammatory agent, preferably wherein the corticosteroid is a glucocorticosteroid; or wherein the anti-inflammatory agent is a non-steroidal anti-inflammatory agent (NSAID) selected from the group consisting of ketoprofen, naproxen, meloxicam, COX-1 inhibitors, and COX-2 inhibitors.

In another embodiment, the glyceride mixture comprises SUP DM, preferably wherein the glyceride mixture comprises castor oil:SUP DM having a relative concentration of 8:1.0, 8:1.1, 8:1.2, 8:1.3, 8:1.4, 8:1.5, 8:1.6, 8:1.7, 8:1.8, 8:1.9, 8:2.0, 8:2.1, 8:2.2, 8:2.3, 8:2.4, or 8:2.5 (w:w).

In another embodiment, less than 80% of the bupivacaine is released from a depot of the semi-solid gel in five days when measured in vitro at 37° C.

In another embodiment, the viscosity is less than 701 cPs at 30° C.

In another embodiment, the pharmaceutical composition releases bupivacaine for at least one week when measured in vitro at 37° C.

In another embodiment, the pharmaceutical composition releases bupivacaine for at least two weeks when measured in vitro at 37° C.

In another embodiment, the glyceride mixture has an aqueous solubility of less than 1 mg/ml or less than 0.1 mg/ml in a buffer of physiological pH at 37° C.

In another aspect of the description, the glyceride mixture comprises (i) castor oil, and the active agents comprise a corticosteroid, an analgesic or an anti-inflammatory agent, preferably wherein the corticosteroid is a glucocorticosteroid, or wherein the anti-inflammatory agent is a non-steroidal anti-inflammatory agent (NSAID) selected from the group consisting of ketoprofen, naproxen, meloxicam, COX-1 inhibitors, and COX-2 inhibitors. Preferably, the glyceride mixture comprises SUP DM, and the glyceride mixture comprises ricinoleic acid triester:SUP DM, 8:1.8 (w:w). Preferably, less than 80% of the bupivacaine is released from a depot of the semi-solid gel in five days when measured in vitro at 37° C., the viscosity is less than 701 cPs at 30° C., the pharmaceutical composition releases bupivacaine for at least one to two weeks when measured in vitro at 37° C., and the glyceride mixture has an aqueous solubility of less than 1 mg/ml or less than 0.1 mg/ml in a buffer of physiological pH at 37° C.

CO Control: castor oil/BUP (92/8),
Gel 001 SupDM: CO/SUP DM/BUP (72/20/8),
Gel 002 SupD: CO/SUP D/BUP (72/20/8),
Gel 003 Wit E85: CO/WIT E85/BUP (72/20/8), and
Gel 004 G4301: CO/G43/01/BUP (72/20/8);

all in PBS, pH 7.4, 37° C. Sensory blockade was evaluated using paw latency response time recording on a 56° C. hotplate.

Figure 6:
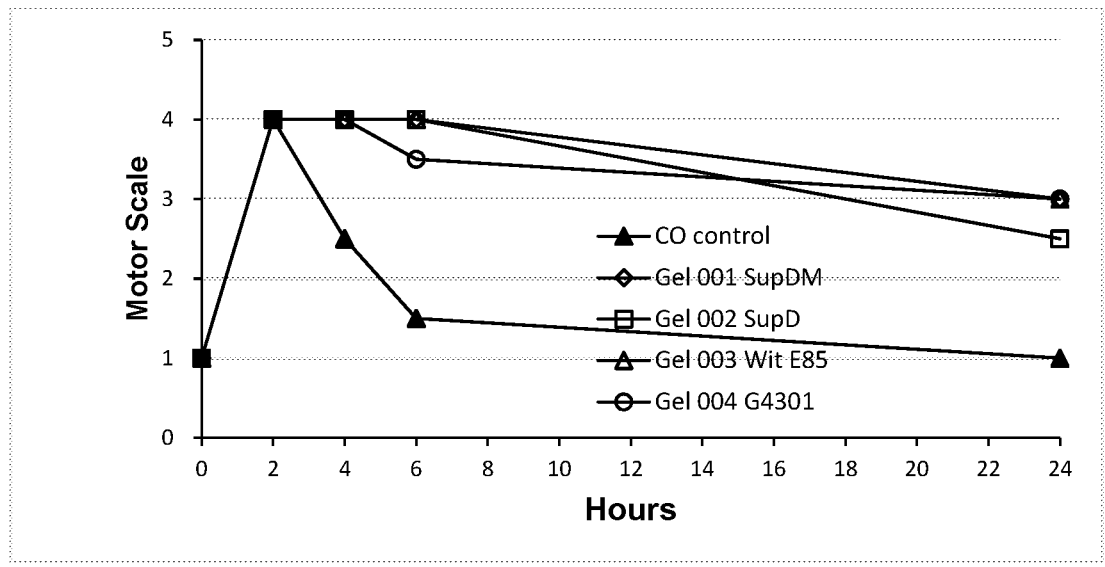
Figure 6A:
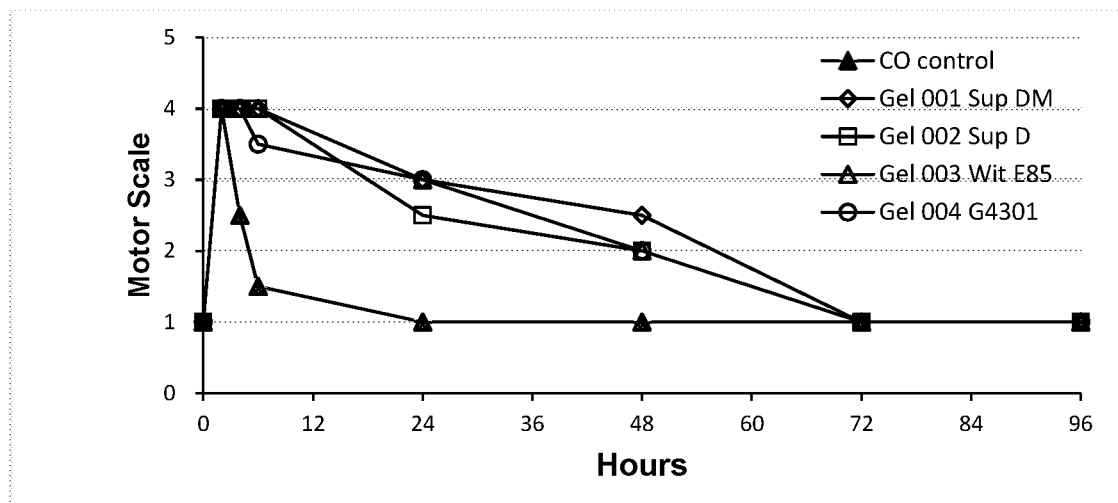
Figure 7:
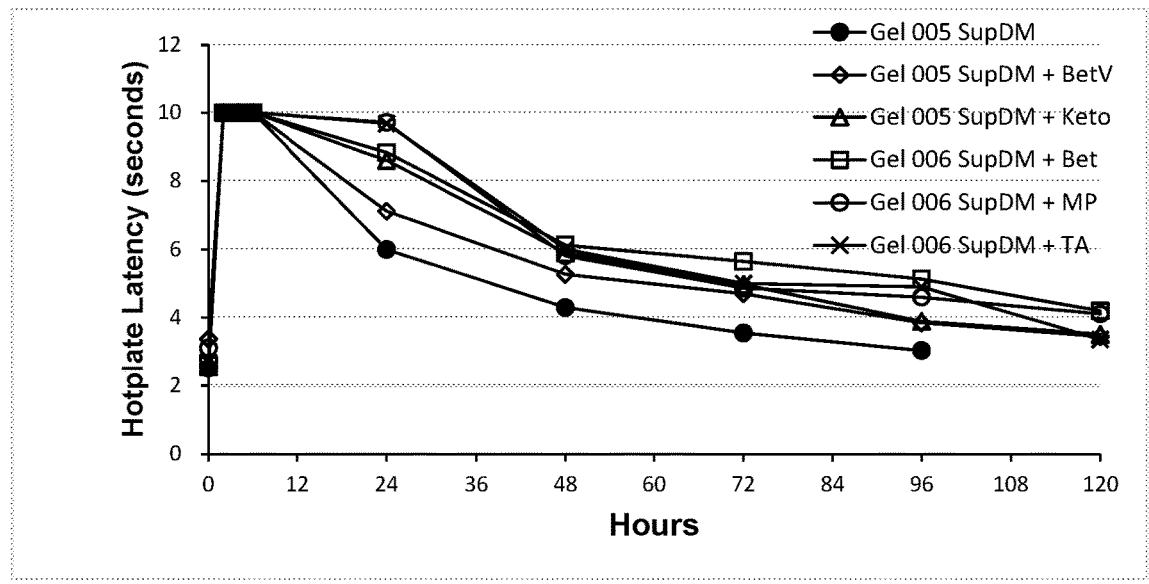

FIGS. 6 and 6a show paw motor ability measurement versus time for a series of bupivacaine castor oil gel formulations, including:

CO Control: Castor oil/BUP (92/8),
Gel 001 SupDM: CO/SUP DM/BUP (72/20/8),
Gel 002 SupD: CO/SUP D/BUP (72/20/8),
Gel 003 Wit E85: CO/WIT E85/BUP (72/20/8), and
Gel 004 G4301: CO/G43/01/BUP (72/20/8);

all in PBS, pH 7.4, 37° C. The paw motor ability test, utilizing a scale of 1 to 4, evaluates the animal's ability to hop and place weight on its hind leg FIG. 7 shows hotplate latencies versus time as a measure of sensory function for a series of bupivacaine with anti-inflammatory castor oil gel formulations, including:

Gel 005 SupDM: CO/SUP DM/BUP (80/12/8),
Gel 005 SupDM+BetV: CO/SUP DM/BUP/BETV (79.95/12/8/0.05),
Gel 005 SupDM+Keto: CO/SUP DM/BUP/KETO (79.85/12/8/0.15),
Gel 006 SupDM+Bet: CO/SUP DM/BUP/BET (71.95/20/8/0.05),
Gel 006 SupDM+MP: CO/SUP DM/BUP/MP (71.85/20/8/0.15), and
Gel 006 SupDM+TA: CO/SUP DM/BUP/TA (71.85/20/8/0.15);

all in PBS, pH 7.4, 37° C. Sensory blockade was evaluated using paw latency response time recording on a 56° C. hotplate.

Figure 8:
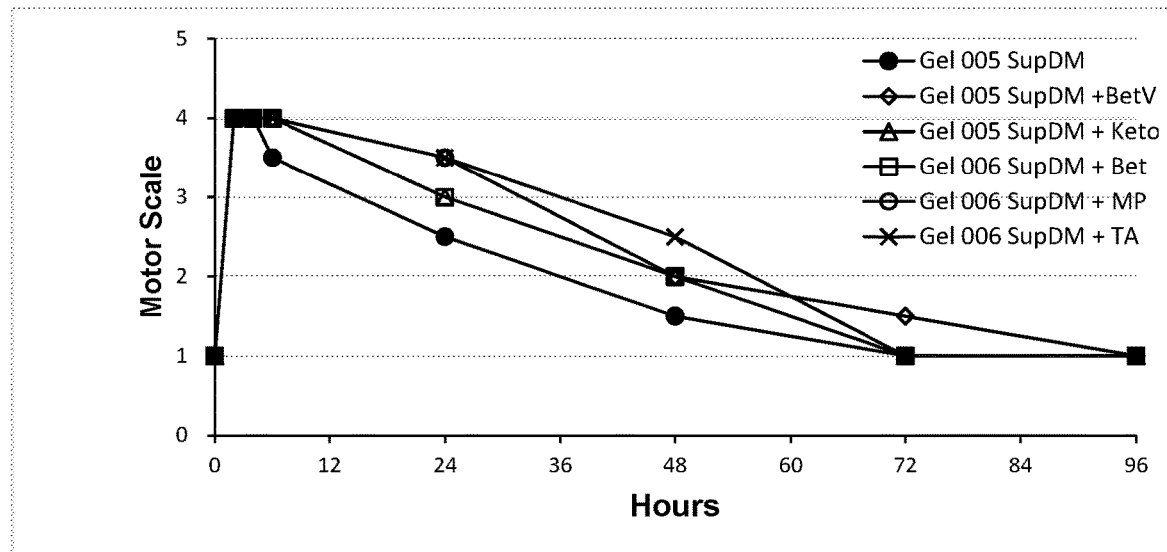

FIG. 8 shows paw motor ability measurement versus time for a series of bupivacaine castor oil gel formulations.

Gel 005 SupDM: CO/SUP DM/BUP (80/12/8),
Gel 005 SupDM+BetV: CO/SUP DM/BUP/BETV (79.95/12/8/0.05),
Gel 005 SupDM+Keto: CO/SUP DM/BUP/KETO (79.85/12/8/0.15),
Gel 006 SupDM+Bet: CO/SUP DM/BUP/BET (71.95/20/8/0.05),
Gel 006 SupDM+MP: CO/SUP DM/BUP/MP (71.85/20/8/0.15),
Gel 006 SupDM+TA: CO/SUP DM/BUP/TA (71.85/20/8/0.15);

all in PBS, pH 7.4, 37° C. The paw motor ability test, utilizing a scale of 1 to 4, evaluates the animal's ability to hop and place weight on its hind leg.

DETAILED DESCRIPTION

Advantages of Bioerodible Semi-solid Gel Technology

The formulations described herein provide a prolonged period of bupivacaine release such that therapeutic concentrations of the drug are achieved rapidly and maintained for at least 72 hours. The potential benefit of the prolonged release profile is to achieve rapid pain relief, maintaining higher levels of active drug at the site of the pain over time to potentially provide greater relief from pain, and to maintain pain relief for 72 hours following surgery.

The animal model studies described herein demonstrate continuous release of the pain-relieving agent bupivacaine for 72 hours.

Benefits of Bioerodible, Semi-solid Gel Technology:

No significant initial burst is found in the formulations described herein. Typically, controlled release injections are associated with an initial burst (higher release of drug immediately after injection). In vitro drug release and animal studies have shown that injectables based on our bioerodible semi-solid gel technology produce less post-injection burst that is typically associated with other commercially available injectable controlled release technologies. For example, NUTROPIN® (somatropin of rDNA origin for injection) has a drug release profile of huge burst followed by very slow drug release.

Drug concentration in the semi-solid gel technology described herein can be as high as 20%, considerably greater than what is typical with other controlled release technologies. For example, a long-acting mepivacaine has been developed using this semi-solid drug delivery technology in which only about 3 wt % of mepivacaine can to be loaded into the polyorthoester vehicle due to the drug's low solubility in the vehicle. In addition, the solubility of bupivacaine in typical vegetable oils is less than 3 wt %. The solubility of bupivacaine in olive oil, corn oil, sesame oil, and vegetable oil were determined to be 2.5 wt %, 2.8 wt %, 3.0 wt % and 2.5 wt % respectively.

The semi-solid gel formulations exhibit described herein have very low viscosity, about 10,000 mPa·s or less at 30° C., preferably 1000 mPa·s or less. Therefore, they can be injected through a small needle such as a 21 G or even a 23 G needle and will exhibit minimal pain (similar to aqueous solution injection) during injection. Additionally, since the semi-solid gel formulations described herein have a higher capacity for drug loading, less volume of drug product is required to be injected. Small injection volumes and low viscosity semi-solid formulations result in easier and less painful administration. Polyorthoester semi-solid formulations have a viscosity of thousands of mPa·s, which is difficult to be injected with a 21 G needle.

The formulations described herein comprise glycerides with natural fatty acids. These compounds are readily hydrolyzed to glycerol and free fatty acids by lipase. These compounds are non-toxic and exhibit excellent biocompatibility in the body. The formulations described herein are biodegradable, bioerodible, and fully resorbable. In animal studies, at two weeks after dosing, no adverse effect of the semi-solid formulation on wound healing was observed. The administration site appeared to be pinkish, and the sciatic nerve appeared to be normal, no inflammation, necrosis, ulceration, or infection was observed.

Compared to microspheres and other polymer-based controlled release injectable systems, the semi-solid gel formulations described herein are readily manufactured at low cost. The active ingredient(s) and semi-solid gel vehicle components are simply mixed at without the use of solvents at relatively low elevated temperatures. Note that since relatively low-melting point solid glycerides (less than 50° C.) (gelling agents) are used, the manufacturing process is at about 60° C.

Further, the formulations described herein can be administered directly for site specific delivery. Since the formulations provide a sustained drug release over a period of days to a month resulting in increased duration of pharmacological action, and reduced frequency of drug administration. The formulations also produce reduced side effects (due to local drug delivery) when compared with systemic administration. The ease of use should produce improved patient compliance.

Definitions

All technical and scientific terms are used herein according to their conventional definitions as they are commonly used and understood by those of ordinary skill in the art of drug delivery. Specific terms for the description herein will be defined below.

"Active agent" includes any locally or systemically acting active agents which may be administered to a subject by topical application or by subcutaneous, subconjunctival, intradermal, intramuscular, intraocular, or intra-articular injection. Examples of these agents include, but not limited to, anti-infectives (including antibiotics, antivirals, fungicides such as itraconazole, scabicides or pediculicides), antiseptics (e.g., benzalkonium chloride, chlorhexidine gluconate, nitrofurazone, or nitromersol), steroids (e.g., estrogens, progestins, androgens, or adrenocorticoids), therapeutic polypeptides (e.g., exenatide, octreotide, insulin, erythropoietin, or morphogenic proteins such as bone morphogenic protein), corticosteroids, analgesics and anti-inflammatory agents (NSAIDs) (e.g., aspirin, ibuprofen, naproxen, ketorolac, indomethacin, meloxicam, COX-1 inhibitors, or COX-2 inhibitors), chemotherapeutic and antineoplastic agents (e.g., paclitaxel, mechlorethamine, cyclophosphamide, fluorouracil, thioguanine, carmustine, lomustine, melphalan, chlorambucil, streptozocin, methotrexate, vincristine, bleomycin, vinblastine, vindesine, dactinomycin, daunorubicin, doxorubicin, or tamoxifen), 5-hydroxytryptophan (serotonin) 3 (5-$HT_3$) receptor antagonists for the prevention and treatment of nausea and vomiting following chemotherapy (e.g., granisetron, ondansetron, or palonosetron), narcotics (e.g., morphine, meperidine, or codeine), antipsychotics including typical antipsychotics (e.g., haloperidol or fluphenazine) and atypical antipsychotics (e.g., risperidone, clozapine, olanzapine, or paliperidone), antiangiogenic agents (e.g., combrestatin, contortrostatin, or anti-vascular endothelial growth factor), polysaccharides, vaccines, antigens, DNA and other polynucleotides, antisense oligonucleotides, or siRNA.

Abbreviations used: bupivacaine, BUT; betamethasone, BET; betamethasone valerate, BETV; ketoprofen, KETO; methylprednisolone, MP; triamcinolone acetonide, TA; meloxicam, MELO.

The present semi-solid formulation described herein may also be applied to other locally acting active agents, such as astringents, antiperspirants, irritants, rubefacients, vesicants, sclerosing agents, caustics, escharotics, keratolytic agents, sunscreens and a variety of dermatologics including hypopigmenting and antipruritic agents.

The term "semi-solid" denotes the physical state of a material that is flowable under a moderate pressure. More specifically, the semi-solid material has a viscosity of less than 10,000 cps (mPa·s) at 30° C.

The term "bioerodible" refers to a material that gradually decomposes, dissolves, hydrolyzes and/or erodes in situ. Generally, the "bioerodible" semi-solid gel described herein are materials that are hydrolizable, and bioerode in situ primarily through both lipolysis and hydrolysis.

The semi-solid lipids, solvent and other agents of the description must be "biocompatible"; that is, they must not cause irritation or necrosis in the environment of use.

The environment of use is a fluid environment and may comprise a subcutaneous, subconjunctival, intramuscular, intravascular (high/low flow), intramyocardial, adventitial, intratumoral, or intracerebral portion, wound sites, tight joint spaces or body cavity of a human or animal.

Castor Oil and Gelling Agents

Castor oil is a preferred triglyceride component of the semi-solid formulations described herein. Castor oil is a triglyceride in which approximately 90% of fatty acid chains are ricinoleates. Oleate and linoleates are the other significant components. Castor oil has been used as a solvent to (emulsify and solubilize other water-insoluble substances) in some injectable pharmaceutical products, but is most widely used in topical formulations, including ophthalmic preparations, where it is used for its emollient effect.

Castor oil is a liquid with a viscosity of approximately 700 cP at 25° C. Although it is a relatively viscous vegetable oil, when a drop of castor oil is added to water or PBS at 37° C., it will immediately spread out and dissipate on the surface of aqueous solution and eventually form small droplets. Therefore, castor oil is not suitable to serve as a sustained release depot.

However, once castor oil is converted to hydrogenated castor oil (castor wax), a hard, high melting point (85 to 88° C.) wax, by the hydrogenation of castor oil using a catalyst, hydrogenated castor wax has been used as an extended release agent in oral and topical pharmaceutical formulations. In oral formulations, hydrogenated castor oil has been used to prepare sustained release tablets and used as capsule lubricant preparations. In topical formulations, it has been used to provide stiffness to creams and emulsions.

Experimental results disclosed below using bupivacaine castor oil solution formulation show that castor oil can only extend bupivacaine's analgesia effect from approximately two hours to four to six hours in a clinically relevant pain model, rat sciatic nerve blockade, due to its relatively high viscosity and relatively slow dissolution of bupivacaine free base into body fluid.

What is disclosed herein is the surprising finding that when a solid gelling agent such as SUPPOCIRE® DM (SUP DM) is added to castor oil, castor oil changes into a soft semi-solid gel. When the SUP DM is at 5%, gelation occurs very slowly at room temperature (flowable at 37° C. body temperature). Gelation occurs at room temperature when SUP DM is at or above 10%. As the amount of SUP DM increase, it takes less time to start gelation. At a 20% level, the semi-solid gel formed is still a soft gel and is injectable with 21 G needle. When the amount of SUP DM increases to 30%, the semi-solid gel formed became a relatively hard gel and is difficult to be injected with a 21 G needle.

The castor oil gels formed are characterized by their property of changing from a fluid at room temperature to a gel at room temperature, and retain as a well-defined gel when the semi-solid gel is placed into in water at 37° C.

In addition, that castor oil slowly released into water, probably due to the cohesive interaction between castor oil and the gelling agent and the relatively hydrophobic semi-solid gel structure. Results herein show the release kinetics of active drugs from formulations comprising CO. A stable gel formulation will ensure the formulation remain as a long-lasting well-defined depot once administrated into the human body to control the gradual release of active drugs and could prevent undesirably rapid release of castor oil into animal or human's bloodstream causing vascular occlusion and potential pulmonary oil microembolism. Furthermore, the low viscosity (approximately 350 cP at 30° C.) nature of the soft semi-solid gel formulation formed can be readily injected through a 21 G needle or applied for local drug delivery.

The gelling agents for the present description are pharmaceutically acceptable and castor oil-compatible materials. As castor oil is a mixture of triglycerides, the solid or semi-solid glycerides are compatible with castor oil to form a semi-solid gel.

More specifically, suitable gelling agents can be solid triglycerides of mixed esters, solid partial glycerides of fatty acids, mixtures of triglyceride, diglyceride or monoglyceride, and other castor oil compatible gelling agents such as sterol ester lanolin. Since these gelling agents are structurally similar to castor oil, they are expected to be compatible. Physically, these materials can be in the form of solid or semi-solid lipid are at room temperature and should also have low solubility with an aqueous solubility of less than 1 mg/mL in physiological pH buffer at 37° C., preferably less than 0.1 mg/mL. If the gelling agents is too hydrophilic and water soluble, it will cause a significant burst of the active drug(s), especially when the active drugs are relatively soluble, which may cause undesirable side effects. If the gelling agent is significantly more insoluble than the main semi-solid lipid, it will retain in the body significantly longer when the active drug and the main semi-solid lipid is completely dissolved and resorbed by the body.

Useful solid or semi-solid lipid compatible with castor oil to form a semi-solid gel delivery vehicle for active drugs include solid triglycerides of mixed esters, solid partial glycerides of fatty acids, mixtures of triglyceride, diglyceride or monoglyceride, and other castor oil compatible gelling agents such as sterol ester lanolin with a melting point of less than 100° C., preferably between 37° C. and 75° C., and more preferably between 37° C. and 50° C. When the melting point gets too high, especially at higher concentration (>20 wt %), it will cause the hardening of the semisolid gel, and affect the injectability of the semi-solid gel formulations.

Solid triglycerides that can be added to castor oil to form a semi-solid gel include SUP DM, a mixture of $C_{12}$ to $C_{18}$ triglycerides with a melting point of 42.5° C. to 46° C.; SUPPOCIRE® D (SUP D), a mixture of $C_{12}$ to $C_{18}$ triglycerides with a melting point of 42° C. to 45° C.; SUPPOCIRE® CM (SUP CM), a mixture of $C_{12}$ to $C_{18}$ triglycerides with a melting point of 37.8° C. to 39.8° C.; SOFTISAN® 378 (S378), a triglycerides of $C_{10}$ to $C_{18}$ fatty acids with a melting point of 39° C. to 42° C.; and hydrogenated castor oil with a melting point of 85° C. to 88°.

Solid partial glycerides of fatty acids that can be added to castor oil to form a semi-solid gel include GELUCIRE 43/01 (G43/01) glyceride of $C_{12}$ to $C_{18}$ fatty acids with a melting point of 42° C. to 45° C.; GELEOL™, a glyceryl monostearate with a melting point of 54° C. to 64° C.; GELUCIRE 39/01 (G39/01) a glyceride mixture of mono-, di-, and triglycerides of $C_{12}$ to $C_{18}$ fatty acids with a melting point of 37° C. to 40° C.; and COMPRITOL® 888 ATO, glyceryl behenate with a melting point of 65° C. to 77° C.

Mixtures of triglyceride, diglyceride or monoglyceride that can be added to castor oil to form a semi-solid gel include WITEPSOL® E85 (WIT E85) with a melting point of 42° C. to 44° C.; and WITEPSOL® E76 (WIT E76) with a melting point of 37° C. to 39° C.

Furthermore, other castor oil compatible gelling agents such as sterol ester lanolin with a melting point of 38° can be added to castor oil to form a semi-solid gel.

The concentrations of gelling agents added to castor oil may vary. For example, the concentration (wt %) of the gelling agents may be in the range of about 8 to 30 wt %, preferably about 10 to 20 wt %.

The castor oil mixed with the gelling agents (the final delivery vehicle), and the delivery vehicle with the active ingredients can form a defined long-lasting depot once administered into the body at 37° C., and will gradually degrade/erode, and be dissolved into the body liquids, and the semi-solid lipids will eventually be hydrolyzed to natural free glycerol and free fatty acids by lipase through a process called lipolysis.

Preparation of Castor Oil Semi-solid Gel Formulation

The castor oil semi-solid gel formulation of an active agent described herein may be prepared by directly mixing together with castor oil and the gelling excipient, or by mixing with the semi-solid gel already formed. The mechanical mixing process is performed at a suitable temperature, typically between 60° C. and 90° C., to completely melt the gelling excipients and castor oil into a solution, and dissolve or mill by any mechanical means the active drugs to from a clear solution or a homogeneous suspension. A vacuum may be applied to avoid air bubbles, and nitrogen may be applied to reduce oxidation of active drugs and the delivery vehicle components. After achieving a homogeneous and uniform pharmaceutical composition, the active agent semi-solid gel formulation can be cooled down to room temperature.

Local Anesthetic Semi-solid Gel Pharmaceutical Compositions

Local anesthetics induce a temporary nerve conduction block, and a local analgesic effect for pain relief in surgical procedures, dental procedures, and injuries.

Clinical local anesthetics belong to one of two classes: amide and ester local anesthetics. Amide local anesthetics include bupivacaine, ropivacaine, levobupivacaine, dibucaine, etidocaine, lidocaine, mepivacaine. Ester local anesthetics include benzocaine, chloroprocaine, cocaine, proparacaine and tetracaine. The local anesthetics may be present as the free base, or as an acid addition salt, or as a mixture thereof. A mixture of two different local anesthetics or a mixture of the same local anesthetics in two forms, the free base form and the acid addition salt, may be used to achieve the desired pharmacological effect and release rate and duration.

The active agents (free base) can be readily converted into a salt with fatty acids and other pharmaceutically acceptable acids. Both saturated and unsaturated fatty acids such as lauric acid, myristic acid, palmitic acid, and oleic acid are natural fatty acids, and can be used. This conversion can increase its compatibility and solubility in the semi-solid vehicle. The selected active agents can be converted into a salt in advance before being incorporated into the semi-solid vehicle or can be added into the semi-solid vehicle simultaneously at a 1:1 molar ratio or other molar ratios during the formulation manufacturing process.

The amount of active agent(s) present in the composition can vary over a wide range depending on a number of factors, such as the therapeutically effective dose of the active drug, the desired duration of biological or therapeutic effect, and the release profile of the composition. The concentration of the active agent may be in the range of about 0.01 to 60 wt %, preferably about 5 to 40 wt %, or more preferably about 5 to 20 wt %.

A corticosteroid, an analgesic or an anti-inflammatory agent can be added to the local anesthetic semi-solid gel formulation; preferably wherein the corticosteroid is a glucocorticosteroid; or wherein the anti-inflammatory agent is a non-steroidal anti-inflammatory agent (NSAID) selected from the group consisting of ketoprofen, naproxen, meloxicam, COX-1 inhibitors, and COX-2 inhibitors. The concentrations of the anti-inflammatories are selected based on the potency of the drugs and their clinical doses. The concentration of the anti-inflammatory may be in the range of about 0.01 to 1 wt %, preferably about 0.03 to 0.5 wt %, or more preferably about 0.03% to 0.15% for local inhibition of inflammation.

The glyceride mixture comprises castor oil:gelling agents is 8:1.0, 8:1.1, 8:1.2, 8:1.3, 8:1.4, 8:1.5, 8:1.6, 8:1.7, 8:1.8, 8:1.9, 8:2.0, 8:2.1, 8:2.2, 8:2.3, 8:2.4, 8:2.5 (w:w).

The concentration (wt %) of the gelling agents may be in the range of about 8 to 30 wt %, preferably about 10 to 20 wt %.

In addition, other pharmaceutically acceptable agents such as penetration enhancers, including natural penetration ingredients such as oleic acid, linoleic acid, and synthetic ingredients such as azone, propylene glycol N-methylpyrrolidone, antioxidants, preservatives, and other inert agents such as coloring or flavoring agents may be added.

This pharmaceutical semi-solid gel composition of the present semi-solid formulation described herein has a smooth semi-solid gel texture. Therefore, the composition can be filled into syringes with a 21 G to 25 G needle for subcutaneous, subconjunctival, intradermal, intramuscular, epidural or intrathecal injection, or can also be conveniently applied onto already-open sites such as surgical wounds/site or exposed skin or mucous membrane.

After administration by injection or topical application, the active agent is released from the composition in a sustained and controlled manner. The rate of release may be regulated in a variety of ways to accommodate the desired duration of therapeutic effect. For example, the rate may be increased or decreased by using different level of gelling agents. It may also be altered by selecting different gelling agents or by changing their amount, or the combination thereof. In addition, lower water solubility forms of active agents such as their base forms, or as complexes with fatty acids may be used to delay the release of active agents.

Pharmaceutical Uses

The local anesthetics semi-solid gel pharmaceutical compositions of the present description can be topically applied onto already-open sites such as skin or mucous membrane or filled into syringes and directly injected into the surgical cavity and at different layers within the wound, such as across the peritoneal incision and directly below the skin incision. This drug product enables localized treatment of both the incisional and deep visceral pain components normally associated with moderate and major surgery. This drug product provides pain relief for the first three days following surgery when pain is most debilitating. This product has the potential to be widely used to manage post-operative pain following moderate/major surgeries, e.g., abdominal, gynecological, thoracic, or orthopedic surgeries.

Other Semi-solid Gel Pharmaceutical Formulations

Exemplary compositions of this semi-solid formulation described herein, and their uses, include: compositions containing ophthalmic drugs, corticosteroid such as loteprednol for the treatment of inflammation of the eye; glaucoma drug such as latanoprost for the treatment of open-angle glaucoma or ocular hypertension; antiangiogenic agents such as combrestatin for the treatment of macular degeneration and retinal angiogenesis; and other compositions for the controlled release of ophthalmic drugs to the eye.

The amount of active agent(s) present in the composition can vary over a wide range depending on a number of factors, such as the therapeutically effective dose of the active drug, the desired duration of biological or therapeutic effect, and the release profile of the composition. The concentration of the active agent may be in the range of about 0.01 to 60 wt %, preferably about 1 to 10 wt %.

The concentration of the main semi-solid lipid may be in the range of about 1 to 99 wt %, preferably about 5 to 80 wt %. The concentration of the first modifying excipient may be in the range of about 1 to 50 wt %, preferably about 5 to 20 wt %. The concentrations of the second type of gelling agents may be in the range of about 0.1 to 10 wt %, preferably about 0.5 to 5 wt %. In addition, other pharmaceutically acceptable agents such as antioxidants, preservatives, and other inert agents such as coloring or flavoring agents may be added.

1. Background a. S701

SOFTIGEN® 701 (S701) is manufactured through transesterification of castor oil with glycerol in the presence of sodium hydroxide. Castor oil (CO) is the starting material for S701. S701 only cause mild/moderate reversible inflammatory response at the administration site, but does not affect wound healing, or scar formation in rat, rabbit, and dog studies.

The inventors found that batches of S701 were inconsistent, i.e., appearance varied from liquid, to partial liquid/partial semi-solid, to semi-solid, or paste, and that this variation affected the physical state and in vitro release of formulations. For example, the in vitro release of a drug is faster if the batch of S701 used is a liquid.

b. Castor Oil (CO)

CO is a consistent material with respect to composition and physical properties such as viscosity. Castor oil is an oil solution, not a sustainable "depot". Upon injection, it can cause vascular occlusion and potential pulmonary oil microembolism, especially using a large bolus (3-5 mL). Rapid release or dumping of relatively large volume of castor oil could become a safety issue.

c. Gelling Agents

One object of studies summarized herein was to change castor oil into a stable gel that controls the release of a solubilized drug, and also controls the release of castor oil into surrounding tissue. Another object was to prevent rapid release of drug and/or dumping of castor oil.

Pharmaceutically acceptable gelling agents were tested. Aluminum salts of fatty acids such as aluminum stearate and magnesium stearate are commonly used. Polymers such as carboxymethyl cellulose, polyvinyl alcohol, and polyvinylpyrrolidone are also used. Polysaccharides such as natural pectin and starches are typically used for aqueous systems, and are not compatible with CO. It was found that pectin from different sources provides different gelling abilities, due to variations in molecular size and chemical composition. Like other natural polymers, a major problem with pectin is inconsistency in reproducibility between samples, which may result in poor reproducibility in drug delivery characteristics.

Gelling experiments were performed as follows. The targeted amounts of gelling agents and the castor oil was weighed and transferred to a glass vial and sealed. The mixture was heated to about 96° C. in a water bath for about ten minutes, and then vortexed for one minute. The procedure was repeated three times with a total of 30 minutes to dissolve the gelling agents into castor oil. Three polymers, carboxymethyl cellulose, polyvinyl alcohol, and polyvinylpyrrolidone were tested at 0.2% level (2 mg of polymer was added to 1 g of castor oil, and heated and vortexed at 96° C. for 30 minutes. None of them were soluble at all in castor oil.

Aluminum distearate was tested at 0.1%, 0.5%, and 1% in castor oil. Results showed that the solubility of aluminum distearate in castor oil was less than 0.1% after being heated and vortexed at 96° C. for 30 minutes. No gel formation occurred when cooled to room temperature overnight.

None of the above "gelling agents" tested were soluble and compatible with CO.

Relatively high melting point glycerides were then tested measuring the time from start gelation and complete gelation, and release of castor oil at 37° C. in water. In vitro, and in vivo studies showed that formulations comprising relatively high melting point glycerides and CO provided significantly better controlled bupivacaine release, and thus improved analgesic efficacy. Further, CO is a triglyceride, and exhibited less inflammation than commercial S701, which is a mixture of mono-, di- and triglycerides.

Addition of an anti-inflammatory agent significantly improved efficacy.

2. Bupivacaine Semi-solid Gel Formulation a. Bupivacaine Solubility in Neat Castor Oil The solubility of bupivacaine in castor oil was determined by dissolving bupivacaine into castor oil by mixing the components at an elevated temperature of 70-80° C. to form a clear solution which resulted as a clear oil solution when cooled down to ambient temperature. Bupivacaine ranging from 5% up to 20% can be readily dissolved into castor oil.

b. Required Amount of SUP DM to Form Castor Oil Gel

The required amount of gelling agent to form a castor oil semi-solid gel formulation in the presence of 8 wt % bupivacaine was determined by mixing the components at an elevated temperature of 70-80° C. form a clear solution while mixing and resulted as a homogeneous semi-transparent or opaque gel formulation after cooling down to room temperature. The results in Table 1 show that gelling agent SUP DM ranging from 10% up to 30% can form a semi-transparent or opaque semi-solid gel formulation.

When the gelling agent SUP DM is at 5%, gelation occurs very slowly at room temperature (flowable at 37° C. body temperature). When SUP DM is at or above 10%, gelation occurs at 21° C. As the amount of SUP DM increase, it takes less time to start gelation. At 20% level, the semi-solid gel formed is still a soft gel and is injectable with 21 G needle. When the amount of SUP DM increases to 30%, the semi-solid gel formed became a relatively hard gel and is difficult to be injected with a 21 G needle. The results suggest that 10% to 20% of SUP DM can be used as a gelling agent to form a nice bupivacaine semi-solid gel formulation with good syringeability.

TABLE 1

Castor oil/gelling agent ratio study:
bupivacaine semi-solid gel formulations

| Sample ID | Castor Oil (g) | SUP DM (g) | Bup Amount (mg) | Required time to start gelation at 21° C. (minutes) | Required time to complete gelation at 21° C. (minutes) |
|---|---|---|---|---|---|
| Gel F01 | 0.87 | 0.05 | 80 | 20:00 | 43:00 |
| Gel F02 | 0.82 | 0.10 | 80 | 10:00 | 21:00 |
| Gel F03 | 0.80 | 0.12 | 80 | 8:30 | 18:00 |

TABLE 1-continued

Castor oil/gelling agent ratio study:
bupivacaine semi-solid gel formulations

| Sample ID | Castor Oil (g) | SUP DM (g) | Bup Amount (mg) | Required time to start gelation at 21° C. (minutes) | Required time to complete gelation at 21° C. (minutes) |
|---|---|---|---|---|---|
| Gel F04 | 0.77 | 0.15 | 80 | 7:45 | 13:00 |
| Gel F05 | 0.72 | 0.20 | 80 | 6:15 | 11:00 |
| Gel F06 | 0.62 | 0.30 | 80 | 5:25 | 8:00 |

The castor oil gels formed are characterized by their property of changing from a fluid at room temperature to a gel at room temperature, and retain as a well-defined gel when the semi-solid gel is placed into in water at 37° C. A castor oil bupivacaine semi-solid gel formulation was prepared with 15% SUP DM when placed and tested in water at 37° C.

In addition, it was observed that castor oil was very slowly released out into water, potentially due to the cohesive interaction between castor oil and the gelling agent and the relatively hydrophobic semi-solid gel structure.

Bupivacaine ranging from 5% up to 15% can be readily dissolved into the semi-solid lipid mixture of castor oil and SUP DM mixture. Although up to 15% of bupivacaine was soluble in the final semi-solid gel formulation mixture, less than 10% was selected to avoid potential drug crystallization during long term storage.

The concentration of bupivacaine is selected based on its potency and clinical doses. The target bupivacaine concentration is 80-130 mg/mL based on the maximum recommended single adult dose of 400 mg bupivacaine hydrochloride (Bupivacaine PI) for a dose volume of 3-5 mL for a typical 10-15 cm length surgical opening.

c. Additional Gelling Agents

Additional castor oil compatible gelling agents suitable to form a bupivacaine semi-solid gel formulation were identified using the above experimental approach. Besides SUP DM, a mixture of $C_{12}$ to $C_{18}$ triglycerides with a melting point of 42.5° C. to 46° C., other solid or semi-solid triglycerides include SUPPOCIRE® D (SUP D), a mixture of $C_{12}$ to $C_{18}$ triglycerides with a melting point of 42° C. to 45° C.; SUPPOCIRE® CM (SUP CM) a mixture of $C_{12}$ to $C_{18}$ triglycerides with a melting point of 37.8° C. to 39.8° C.; SOFTISAN® 378 (S378), a triglycerides of $C_{10}$ to $C_{18}$ fatty acids with a melting point of 39° C. to 42° C.; and hydrogenated castor oil with a melting point of 85° C. to 88° C. These were also tested as gelling agents to enable castor oil to form semi-solid gel formulations in the presence of bupivacaine.

The semi-solid local anesthetic pharmaceutical compositions below were prepared as follows: The local anesthetics, castor oil, and gelling agents were added to a glass container, and then heated to about 60° C. to 90° C. depending on the properties of local anesthetics and the vehicle components used to completely melt semi-solid lipid and gelling agents into a solution, and completely dissolve the active drugs into the delivery vehicle to from a clear solution while mixing. After achieving a homogeneous and uniform pharmaceutical composition, the local anesthetic semi-solid formulation can be cooled down to ambient temperature naturally.

EXAMPLES

Commercial products were used according to Table 2, which are available in GMP quality and quantity.

TABLE 2

Commercial triglyceride mixtures

| Castor oil | ricinoleic acid triglycerides |
|---|---|
| SUPPOCIRE ® DM (SUP DM) | a mixture of $C_{12}$ to $C_{18}$ triglycerides with a melting point of 42.5° C. to 46° C. |
| SUPPOCIRE ® D (SUP D) | a mixture of $C_{10}$ to $C_{18}$ triglycerides with a melting point of 42° C. to 45° C. |
| SUPPOCIRE ® CM (SUP CM) | a mixture of $C_{12}$ to $C_{18}$ triglycerides with a melting point of 37.8° C. to 39.8° C. |
| SOFTISAN ® 378 (S378) | a mixture of $C_{10}$ to $C_{18}$ triglycerides with a melting point of 39° C. to 42° C. |
| GELUCIRE 43/01 (G43/01) | a mixture of $C_8$ to $C_{18}$ triglycerides with a melting point of 42° C. to 45° C. |
| GELUCIRE 39/01 (G39/01) | a mixture of $C_{12}$ to $C_{18}$ triglycerides with a melting point of 37° C. to 40° C. |
| GELEOL ™ (GEL) | a glyceryl monostearate with a melting point of 54° C. to 64° C. |
| COMPRITOL ® 888 ATO (COM) | glyceryl behenate with a melting point of 65° C. to 77° C. |
| WITEPSOL ® E 85 (WIT E85) | hydrogenated coco-glycerides with a melting point of 42° C. to 44° C. |
| WITEPSOL ® E 76 (WIT E76) | Hydrogenated coco-glycerides with a melting point of 37° C. to 39° C. |
| SOFTIGEN ® 701 (S701) | ricinoleic acid partial glycerides |

Example 1. SUP D

The SUP D mixture of $C_{12}$ to $C_{18}$ triglycerides has a melting point of 42° to 45° C. The CO and SUP D ratio study is shown in Table 3. The targeted amount of each component was weighed to a glass vial and heated to about 75° C. in a water bath, and mixed/vortexed until all components are completely dissolved and form a clear solution.

It takes about the same time for SUP DM and SUP D to start and complete gelation because they exhibit similar properties and melting points. Approximately 1 mL of the hot solution was filled into a 5 mL prefilled syringe, and steam-sterilized under 121° C. for 20 minutes. They appeared as a homogeneous opaque gel with or without steam sterilization after cooling down to room temperature at 10 to 20 wt % gelling agent level, and are injectable with 21 G needle.

TABLE 3

CO and SUP D ratio study

| Sample ID | CO (g) | SUP D (g) | BUP (mg) |
|---|---|---|---|
| SUP D F01 | 1.64 | 0.20 | 160 |
| SUP D F02 | 1.54 | 0.30 | 160 |
| SUP D F03 | 1.44 | 0.40 | 160 |

Example 2. SUP CM

The SUP CM mixture of $C_{12}$ to $C_{18}$ triglycerides has a melting point of 37.8 to 39.8° C. The CO and SUP CM ratio study is shown in Table 4. The targeted amount of each component was weighed to a glass vial and heated to about 75° C. in a water bath, and mixed/vortexed until all components are completely dissolved and form a clear solution.

It takes longer for SUP CM than those for SUP DM to start and complete gelation because SUP CM has lower melting point.

Approximately 1 mL of the hot solution was filled into a 5 mL prefilled syringe, and steam-sterilized under 121° C. for 20 minutes. They appeared as a homogeneous opaque gel with or without steam sterilization after cooling down to room temperature at 10 to 20 wt % gelling agent level, and are injectable with 21 G needle.

TABLE 4

CO and SUP CM ratio study

| Sample ID | CO (g) | SUP CM (g) | BUP (mg) |
|---|---|---|---|
| SUP CM F01 | 1.64 | 0.20 | 160 |
| SUP CM F02 | 1.54 | 0.30 | 160 |
| SUP CM F03 | 1.44 | 0.40 | 160 |

Example 3. S378

The S378 mixture of triglycerides of $C_{10}$ to $C_{18}$ fatty acids has a melting point of 39° to 42° C. and is in the form of a semi-solid. Its gelling power is less than those in the form of hard solid, higher amount/concentration compared to other solid triglyceride was used. At 40 wt % S378 level, it takes about 6:30 minutes to start gelation, but 36:00 minutes to complete gelation.

The CO and S378 ratio study is shown in Table 5. The targeted amount of each component was weighed to a glass vial and heated to about 75° C. in a water bath, and mixed/vortexed until all components are completely dissolved and form a clear solution.

Approximately 1 mL of the hot solution was filled into a 5 mL prefilled syringe, and steam-sterilized under 121° C. for 20 minutes. They appeared as a homogeneous opaque gel with or without steam sterilization after cooling down to room temperature at 30 to 50 wt % gelling agent level, and are injectable with 21 G needle. At 20% level, the formulation is still flowable after cooling down to room temperature.

TABLE 5

CO and S378 ratio study

| Sample ID | CO (g) | S378 (g) | BUP (mg) |
|---|---|---|---|
| S378 F01 | 1.44 | 0.40 | 160 |
| S378 F02 | 1.24 | 0.60 | 160 |
| S378 F03 | 1.04 | 0.80 | 160 |
| S378 F04 | 0.84 | 1.00 | 160 |

Example 4. HCO

Hydrogenated castor oil solid triglyceride (HCO) has a relatively high melting point of 85 to 88° C. Due to its high melting point, this gelling agent need to be heated above 88° C. to be completely melted and homogeneously mixed with castor oil to form a semi-solid gel.

The CO and HCO ratio study is shown in Table 6. The targeted amount of each component was weighed to a glass vial and heated to about 90° C. in a water bath, and mixed/vortexed until all components are completely dissolved and form a clear solution. Approximately 1 mL of the hot solution was filled into a 5 mL prefilled syringe, and steam-sterilized under 121° C. for 20 minutes. They appeared as a homogeneous opaque gel with or without steam sterilization after cooling down to room temperature at 10 to 20 wt % gelling agent level and are injectable with 21 G needle at 10 and 15 wt % level. At 20% level, it takes 1:25 minutes to start gelation, and 5 minutes to complete gelation. The formulation became a relatively hard gel and is difficult to be injected with a 21 G needle.

TABLE 6

CO and HCO ratio

| Sample ID | CO (g) | HCO (g) | BUP (mg) |
|---|---|---|---|
| HCO F01 | 1.64 | 0.20 | 160 |
| HCO F02 | 1.54 | 0.30 | 160 |
| HCO F03 | 1.44 | 0.40 | 160 |

Solid partial glycerides of fatty acids include G43/01, a mixture of $C_8$ to $C_{18}$ triglycerides with a melting point of 42° C. to 45° C.; GELEOL™, a glyceryl monostearate with a melting point of 54° C. to 64° C.; COM, a glyceryl behenate with a melting point of 65° C. to 77° C.; and G39/01, a glyceride mixture of mono-, di-, and triglycerides of $C_{12}$ to $C_{18}$ fatty acids with a melting point of 37° C. to 40° C. These were tested as gelling agents to enable castor oil to form semi-solid gel formulations in the presence of bupivacaine.

Example 5. G43/01

The G43/01 mixture of $C_8$ to $C_{18}$ triglycerides has a melting point of 42 to 45° C. The CO and G43/01 ratio study is shown in Table 7. The targeted amount of each component was weighed to a glass vial and heated to about 75° C. in a water bath, and mixed/vortexed until all components are completely dissolved and form a clear solution.

It takes about 8:30 minutes and 6:30 minutes to start gelation, and 15:00 minutes and 13:00 minutes to complete gelation for 15% and 20% G43/01 respectively.

Approximately 1 mL of the hot solution was filled into a 5 mL prefilled syringe, and steam-sterilized under 121° C. for 20 minutes. They appeared as a homogeneous opaque gel with or without steam sterilization after cooling down to room temperature at 10 to 20 wt % gelling agent level, and are injectable with 21 G needle.

TABLE 7

CO and G43/01 ratio study

| Sample ID | CO (g) | G43/01 (g) | BUP (mg) |
|---|---|---|---|
| G43/01 F01 | 1.64 | 0.20 | 160 |
| G43/01 F02 | 1.54 | 0.30 | 160 |
| G43/01 F03 | 1.44 | 0.40 | 160 |

Example 6. COM

The CO and COM ratio study is shown in Table 8. This solid glyceryl behenate has a melting point of 65 to 77° C. The targeted amount of each component was weighed to a glass vial and heated to about 80° C. in a water bath, and mixed/vortexed until all components are completely dissolved and form a clear solution.

Approximately 1 mL of the hot solution filled into a 5 mL prefilled syringe, and steam-sterilized under 121° C. for 20 minutes. It appeared as a homogeneous opaque gel with or without steam sterilization after cooling down to room temperature at 10 to 20 wt % gelling agent level. It is injectable with 21 G needle at 10 and 15 wt % level. At 20% level, the formulation became a relatively hard gel and is not injectable with a 21 G needle.

TABLE 8

CO and COM ratio study

| Sample ID | CO (g) | COM (g) | Bup Amount (mg) |
|---|---|---|---|
| Com F01 | 1.64 | 0.20 | 160 |
| Com F02 | 1.54 | 0.30 | 160 |
| Com F03 | 1.44 | 0.40 | 160 |

Example 7. GEL

The CO and GEL ratio study is shown in Table 9. This solid glyceryl monostearate has a melting point of 54 to 64° C. The targeted amount of each component was weighed to a glass vial and heated to about 75° C. in a water bath, and mixed/vortexed until all components are completely dissolved and form a clear solution.

Approximately 1 mL of the hot solution was filled into a 5 mL prefilled syringe, and steam-sterilized under 121° C. for 20 minutes. They appeared as a homogeneous opaque gel with or without steam sterilization after cooling down to room temperature at 10 to 20 wt % gelling agent level, and are injectable with 21 G needle.

TABLE 9

CO and GEL ratio study

| Sample ID | CO (g) | GEL (g) | BUP (mg) |
|---|---|---|---|
| Gel F01 | 1.64 | 0.20 | 160 |
| Gel F02 | 1.54 | 0.30 | 160 |
| Gel F03 | 1.44 | 0.40 | 160 |

Example 8. WIT E85 and WIT E76

Mixtures of triglyceride, diglyceride or monoglyceride such as WIT E85 with a melting point of 42° C. to 44° C., and WIT E76 with a melting point of 37° C. to 39° C., were tested as gelling agents to enable castor oil to form semi-solid gel formulations in the presence of bupivacaine.

The CO and WIT E85 ratio study is shown in Table 10. The targeted amount of each component was weighed to a glass vial and heated to about 75° C. in a water bath, and mixed/vortexed until all components are completely dissolved and form a clear solution.

It takes about 8:30 minutes and 6:30 minutes to start gelation, and about 15:00 minutes and 13:30 minutes to complete gelation.

Approximately 1 mL of the hot solution was filled into a 5 mL prefilled syringe, and steam-sterilized under 121° C. for 20 minutes. They appeared as a homogeneous opaque gel with or without steam sterilization after cooling down to room temperature at 10 to 20 wt % gelling agent level, and are injectable with 21 G needle.

TABLE 10

CO and WIT E85 ratio study

| Sample ID | CO (g) | WIT E85 (g) | BUP (mg) |
|---|---|---|---|
| Wit F01 | 1.64 | 0.20 | 160 |
| Wit F02 | 1.54 | 0.30 | 160 |
| Wit F03 | 1.44 | 0.40 | 160 |

Example 9. Natural Sterol Esters, Lanolin (LAN)

LAN is an "ester", structurally similar to "glyceryl ester", and is compatible with triglyceride castor oil. It has a melting point of 38°. At 18 wt % LAN, it takes about 3:30 minutes to start gelation, but 7:00 minutes to complete gelation due to its high viscosity.

The CO and LAN ratio study is shown in Table 11. The targeted amount of each component was weighed to a glass vial and heated to about 75° C. in a water bath, and mixed/vortexed until all components are completely dissolved and form a clear solution.

Approximately 1 mL of the hot solution was filled into a 5 mL prefilled syringe, and steam-sterilized under 121° C. for 20 minutes. They appeared as a homogeneous opaque gel with or without steam sterilization after cooling down to room temperature at 10 to 20 wt % gelling agent level, and are injectable with 21 G needle.

TABLE 11

CO and LAN ratio study

| Sample ID | CO (g) | LAN (g) | BUP (mg) |
|---|---|---|---|
| Lan F01 | 1.64 | 0.20 | 160 |
| Lan F02 | 1.54 | 0.30 | 160 |
| Lan F03 | 1.44 | 0.40 | 160 |

Example 10. Loteprednol Etabonate

Loteprednol (chloromethyl 17-ethoxycarbonyloxy-11-hydroxy-10,13-dimethyl-3-oxo-7,8,9,11,12,14,15,16-octahydro-6H-cyclopenta[a]phenanthrene-17-carboxylate) (AL-REX® or LO 1'EMAX®) in the form of the ester loteprednol etabonate is a corticosteroid used in ophthalmology. Ocular applications for this drug include the treatment of inflammation of the eye due to allergies (according to the prescription information sheet), as well as chronic forms of keratitis (e.g., adenoviral or Thygeson's keratitis), vernal keratoconjunctivitis, pingueculitis, and episcleritis. The drug has little or no effect on intraocular pressure.

The semi-solid formulation, Gel 001 Lote: CO/SUP DM/loteprednol (77.8/19.5/2.7), was prepared by weighing castor oil, SUP DM and the drug into a glass vial, and closing the lid. The vehicle components were melted by heating to 90° C. in a water bath, and loteprednol was dissolved to form a clear solution and became a semi-transparent soft paste after cooling down to room temperature.

Example 11. Latanoprost

Latanoprost (XALATAN) is used for treating glaucoma or ocular hypertension by reducing intraocular pressure.

The semi-solid formulation, Gel 001 Lata: CO/SUP DM/Latanoprost (80/15/5), was prepared by weighing castor oil, SUP DM and the drug into a glass vial, and closing the lid. The vehicle components were melted by heating to 90° C. in a water bath, and latanoprost was dissolved to form a clear solution and became a semi-transparent soft gel after cooling down to room temperature.

Example 12. In Vitro Release

The semi-solid local anesthetic semi-solid pharmaceutical compositions below were prepared as follows: The local anesthetics, castor oil, and gelling agents, were added to a glass container, and then heated to about 70° C. to 90° C. to completely melt the gelling agents into a solution, and completely dissolve the active drugs into the delivery vehicle to from a clear solution while mixing. After achieving a homogeneous and uniform pharmaceutical composition, the local anesthetic semi-solid formulation was then cooled down to ambient temperature naturally. The semi-solid formulations described herein appeared as a semi-transparent or opaque soft gel.

CO Control: CO/BUP (92/8)
Gel 001 SupDM12: CO/SUP DM/BUP (80/12/8)
Gel 002 SupDM20: CO/SUP DM/BUP (72/20/8)
Gel 003 SupDM30: CO/SUP DM/BUP (62/30/8)
Gel 004 SupD: CO/SUP D/BUP (77/15/8)
Gel 005 Wit E85: CO/WIT E85/BUP (77/15/8)
Gel 006 G4301: CO/G4301/BUP (77/15/8)
Gel 007 HCO: CO/HCO/BUP (80/12/8)

Gel 008 S378: CO/S378/BUP (52/40/8)
Gel 009 Lan: CO/LAN/BUP (74/18/8)
Gel 010 Azone: CO/SUP DM/BUP/Azone (77.5/12/8/2.5)
Gel 001 Lote: CO/SUP DM/loteprednol (77.8/19.5/2.7)
Gel 001 Lata: CO/SUP DM/latanoprost (80/15/5)

The in vitro release profiles of bupivacaine were evaluated by placing approximately 50 mg of the formulation enclosed in porous membrane into a glass bottle with 100 mL of PBS at pH 7.4 without stirring. At various time points, samples were taken and analyzed for bupivacaine content by UV-Vis at 220 nm, for loteprednol by UV-Vis at 277 nm, and for latanoprost by UV-Vis at 210 nm.

The drug release profiles of all the listed semi-solid compositions are summarized in the FIGS. 1 to 4.

The bupivacaine castor oil gel formulations were intended to achieve rapid and sustained pain relief by delivering effective bupivacaine levels at the site for up to 72 hours following surgery. The semi-solid gel is expected to deliver comparable bupivacaine level at an appropriate dose volume (up to 3-5 mL) for a regular 10-15 cm length surgical opening, and at the end of delivery, the semi-solid lipid gel is dissolved/eroded and absorbed. The immediate and rapid local pain relief was resulted from dissolving of the bupivacaine on the formulation surface when aqueous media diffuse into the semi-solid gel. As aqueous media penetrates into the semi-solid lipid gel, the semi-solid lipid erodes, both by surface and bulk erosion, and gradually dissolve into the surrounding aqueous media, bupivacaine will gradually diffuse out and released into the surrounding aqueous media in a sustained manner over a period of time.

Figure 1:
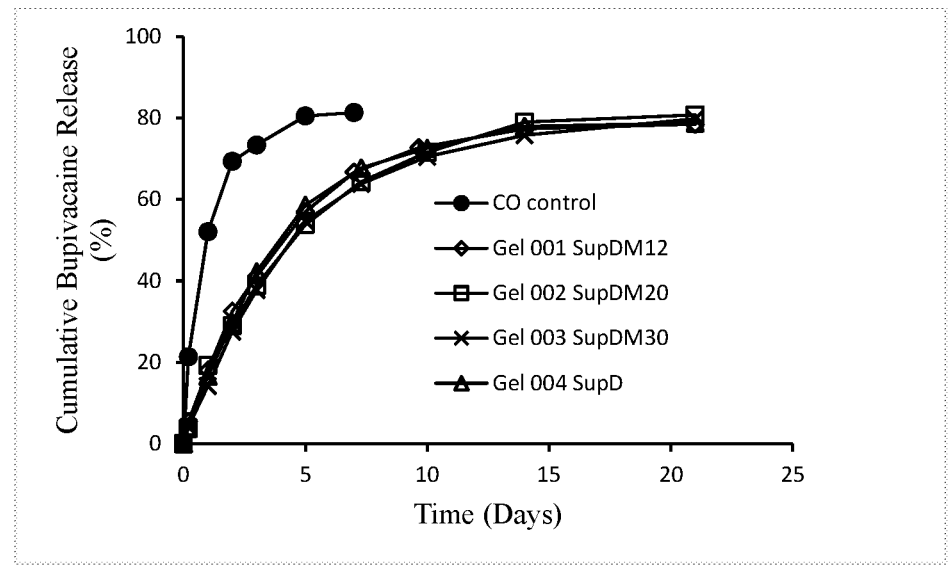
FIG. 1 shows bupivacaine release from castor oil gel formulations gelled by different levels of SUP DM and SUP D, including:
  CO Control: Castor oil/BUP (92/8),
  Gel 001 SupDM12: CO/SUP DM/BUP (80/12/8),
  Gel 002 SupDM20: CO/SUP DM/BUP (72/20/8),
  Gel 003 SupDM30: CO/SUP DM/BUP (62/30/8), and
  Gel 004 SupD: CO/SUP D/BUP (77/15/8);
all in PBS, pH 7.4, 37° C.

As shown in FIG. 1, a bupivacaine castor oil solution formulation containing 8 wt % bupivacaine was used as a control formulation. Castor oil bupivacaine oil solution yielded a significant burst of more than 20% at 4 hours under static condition (without stirring) and more than 50% at 24 hours, and almost 70% at 48 hours. After an additional 10% release from Day 2 to Day 5, the in vitro release curve becomes flatten. Note that lower than 100% recovery is due to the filtration loss of bupivacaine during sample preparation and inaccuracy of UV-Vis method. The poor bupivacaine release kinetics from castor oil was capable of extending analgesic response of approximately 4-6 hours in the rat sciatic nerve blockade model, thanks to its relatively high viscosity and relatively slow dissolution of bupivacaine free base into body fluid.

Figure 2:
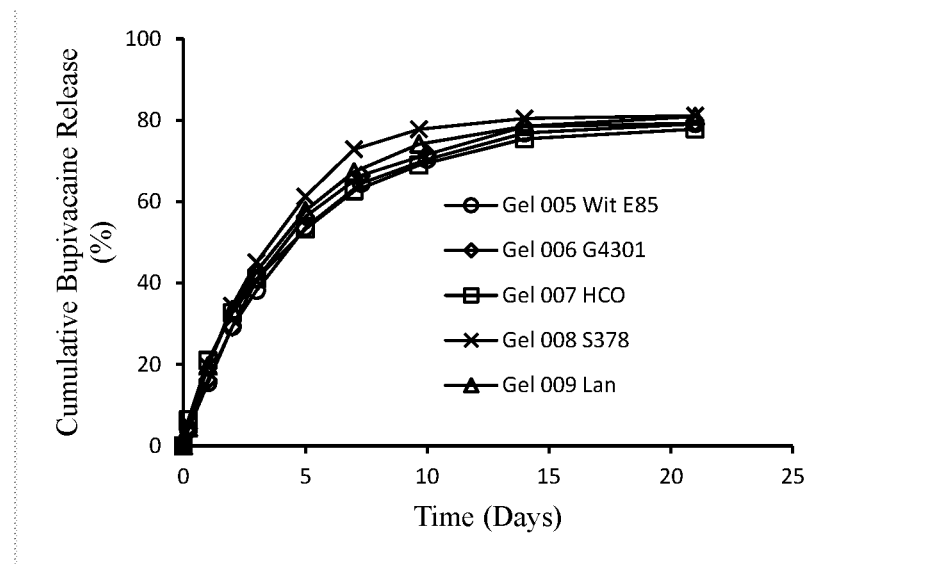
FIG. 2 shows bupivacaine release from castor oil gel formulations gelled by WIT E85, G43/01, hydrogenated castor oil, S378 and lanolin, including:
  Gel 005 Wit E85: CO/WIT E85/BUP (77/15/8),
  Gel 006 G4301: CO/G4301/BUP (77/15/8),
  Gel 007 HCO: CO/HCO/BUP (80/12/8),
  Gel 008 S378: CO/S378/BUP (52/40/8), and
  Gel 009 Lan: CO/Lan/BUP (74/18/8);
all in PBS, pH 7.4, 37° C.

Once castor oil is gelled by either SUP DM ranging from 12%-30% and SUP D, only about 5% of bupivacaine was released at 4 hours, 16-18% at 24 hours, 27-32% at 48 hours, and 54-58% at Day 5. Due to the higher hydrophobicity of the two gelling agents and stable gel depot structure, bupivacaine is gradually released into the surrounding aqueous As shown in FIG. 2, bupivacaine castor oil gel formulations gelled by WIT E85, G43/01, HCO, S378 and LAN, only about 5% of bupivacaine was released at 4 hours, less than 20% at 24 hours, 29-34% at 48 hours, and 53-61% at Day 5. All the five gelling agents are very hydrophobic and can retard the penetration of water into the gel depot and slow the release of bupivacaine. Due to the low melting point of S378 and LAN, the gel depot formed is softer, and bupivacaine release is slightly faster. Again, for the 5 bupivacaine castor oil gel formulations, bupivacaine is gradually released into the surrounding aqueous media in a sustained manner over a 2-3 weeks.

Figure 3:
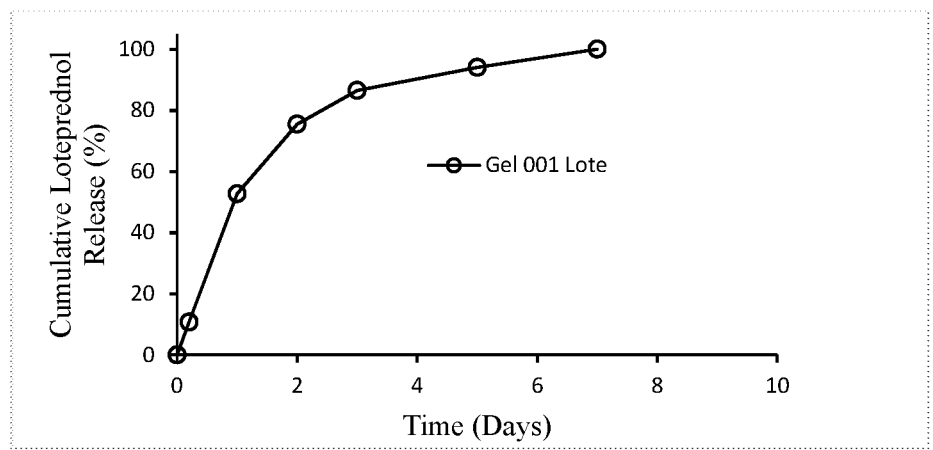
FIG. 3 shows loteprednol release from castor oil gel formulation gelled by SUP DM. Gel 001 Lote: CO/SUP DM/loteprednol (77.8/19.5/2.7); in PBS, pH 7.4, 37° C.

FIG. 3 shows loteprednol etabonate release from castor oil gel formulation gelled by SUP DM, yielding loteprednol release profile for 7 days since loteprednol etabonate is relatively water soluble.

Figure 4:
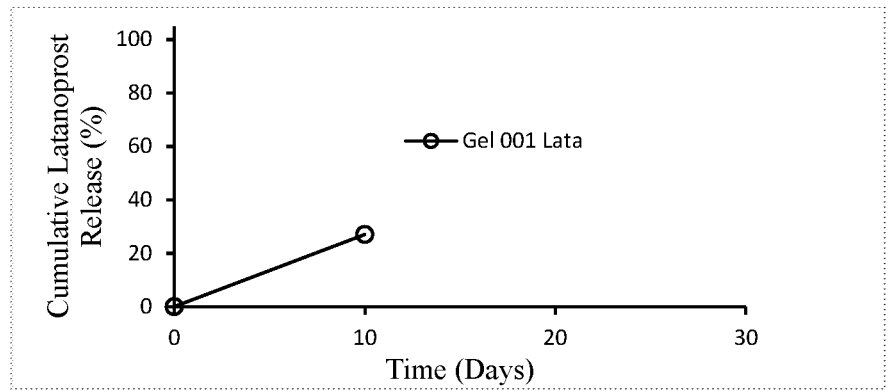
FIG. 4 shows latanoprost release from castor oil gel formulation gelled by SUP DM. Gel 001 Lata: CO/SUP DM/latanoprost (80/15/5); in PBS, pH 7.4, 37° C.

FIG. 4 shows latanoprost release from castor oil gel formulation gelled by SUP DM. Latanoprost is a very hydrophobic drug and only 27% was released at Day 10. Latanoprost is released in vitro in a sustained manner over a month.

Mechanism for Controlled Release of the Formulations Described Herein

When the semi-solid gel formulation is placed into an aqueous environment, water will diffuse into the semi-solid lipid matrix, the active agent on the formulation surface will first gradually dissolve into the surrounding aqueous media. As aqueous media penetrates into the semi-solid lipid gel, the semi-solid lipid erodes, both by surface and bulk erosion, and gradually dissolve into the surrounding aqueous media, the active agent will gradually diffuse out and released into the surrounding aqueous media in a sustained manner over a period of time.

Factors that Affect the Drug Release Rate

The release rate of active agent is affected both by the semi-solid gel vehicle components and the active ingredient and can be regulated in a variety ways to accommodate the desired duration of therapeutic effect.

For the semi-solid gel vehicles, the release rate of active agent can be increased or decreased by using different types/levels/amounts/ratios hydrophobic glyceride gelling agents with different water solubility and/or dissolution rates. As water solubility and dissolution rate of the semi-solid lipids decrease, it will take longer for the semi-solid gel to be dissolved and absorbed, thus resulting longer duration of drug release as long as the active agent exhibits sufficient low solubility.

In addition, lower water solubility forms of active agents such as their base forms, or as complexes with fatty acids may be used to delay the release of active agents.

Bupivacaine can be in the form of a free base or a salt such as bupivacaine hydrochloride which is widely marketed in commercial products under various trade names, including MARCAINE™, SENSORCAINE® and VIVACAINE®. The hydrochloride (HCl) salt of bupivacaine has a water solubility of 600 mg/mL (BASF MSDS sheet), while the free base form of bupivacaine has a predicted water solubility of 0.0977 mg/mL (DrugBank data). In addition, if there is a need to further decrease the water solubility of the drug bupivacaine, one can convert the bupivacaine into a salt with fatty acids and other low solubility acids.

Example 13. Viscosity Determination

This purpose of the viscosity measurement for the semi-solid formulations is to demonstrate that the semi-solid formulations disclosed herein have a very low viscosity and are readily injectable through a 23 G to 21 G needle.

Viscosity Determination Procedure:

The viscosity of the semi-solid formulations was determined on a calibrated Brookfield RVDV-I Prime CP model viscometer using cone spindle CPE-51. The semi-solid formulation samples stored in sealed glass vials were first heated to about 40° C. to 50° C. in an oven until the samples became a flowable viscous liquid. Then approximately 0.5 gram of each sample was weighed into the center the warmed sample cup. Avoid bubbles when possible. Attach the sample cup to the viscometer and measure the viscosity at an appropriate speed of rotation so that the percentage torque is between 10% and 100%. Record the viscosity and percentage torque at the target temperature. Due to the soft paste nature of these materials at room temperature, the viscosity of semi-solid formulations was determined at 30°

C. at that point the semi-solid formulations become a flowable viscous liquid/semi-solid under pressure. Centipoise (cP) and milliPascal seconds (mPa·s) are the CGS and SI units for viscosity. 1 cP=1 mPa·s. The viscosity of all the semi-solid formulations was measured at 30° C.

Viscosity Data

Superior Physiochemical Profile—Low-viscosity Gel Formulations

Castor oil is a liquid with a viscosity of approximately 700 cP at 25° C. and 451 cP at 30° C.

The viscosity value of bupivacaine castor oil gel formulations with and without anti-inflammatory exhibited low viscosity characteristics, ranging from 161 cPs to 701 cPs, with the majority of them below 400 cPs at 30° C. The gelling agents served two roles, one is to gel castor oil, the other is to reduce formulation viscosity to improve syringeability and injectability.

Even these formulations are in the form of gel, they are readily injected through a 21 G needle allowing for a single easy instillation administration (with or without a needle) into the incision site.

Viscosity Values of Bupivacaine Castor Oil Gel Formulation

The viscosity results for the bupivacaine castor oil gel formulations with and without anti-inflammatory were summarized in Table 12. The viscosity of all the semi-solid formulations was measured at 30° C.

TABLE 12

Viscosity results for bupivacaine castor oil gel formulations with and without anti-inflammatory

| Gel formulation composition (wt %) | Viscosity (cP) at 30° C. |
|---|---|
| CO/SUP DM/BUP (82/10/8) | 383 |
| CO/SUP DM/BUP (81/11/8) | 376 |
| CO/SUP DM/BUP (80/12/8) | 365 |
| CO/SUP DM/BUP/BET (76.95/15/8/0.05) | 340 |
| CO/SUP DM/BUP/BETV (76.95/15/8/0.05) | 342 |
| CO/SUP DM/BUP/KETO (76.85/15/8/0.15) | 345 |
| CO/SUP DM/BUP (72/20/8) | 298 |
| CO/SUP DM/BUP/MP (71.85/20/8/0.15) | 300 |
| CO/SUP DM/BUP/TA (71.85/20/8/0.15) | 301 |
| CO/SUP DM/BUP (62/30/8) | 251 |
| CO/SUP D/BUP (77/15/8) | 320 |
| CO/SUP D/BUP (72/20/8) | 287 |
| CO/WIT E85/BUP (77/15/8) | 342 |
| CO/WIT E85/BUP (72/20/8) | 325 |
| CO/G43/01/BUP (77/15/8) | 352 |
| CO/G43/01/BUP (72/20/8) | 300 |
| CO/S378/BUP (52/40/8) | 161 |
| CO/Lan/BUP (77/15/8) | 701 |
| CO/HCO/BUP (82/10/8) | N/A |

The CO/HCO/bupivacaine (82/10/8) formulation is not completely melted at 60° C. due to the high melting point component of HCO, and its viscosity was not determined.

The viscosity value of bupivacaine castor oil gel formulations with and without anti-inflammatory exhibited low viscosity characteristics, ranging from 161 cPs to 701 cPs, with the majority of them below 400 cPs at 30° C. All the gelling agents except lanolin are waxy solids and acts as lubricant due to the waxy property from the long alkyl chains of fatty acids to reduce the viscosity of gel formulations. The active ingredient bupivacaine can also act as a plasticizer and reduce the viscosity of the gel formulations. The very small amounts of anti-inflammatory drugs typically do not affect the viscosity of the gel formulations.

All the bupivacaine castor oil gel formulations with and without anti-inflammatory listed in Table 12 are readily injectable with mechanical pressure (shear force) with a 21 G needle.

The CO/HCO/bupivacaine (82/10/8) formulation is not completely melted at 60° C. due to the high melting point component of HCO, and its viscosity was not determined. However, this formulation is still injectable with a 21 G needle.

Example 14. Evaluation of Skin Reactions

The following bupivacaine castor oil gel formulations with and without anti-inflammatory along with previously developed semi-solid formulations using S701 were administered to each animal by subcutaneous injection at the cleanly shaved dorsal aspect of the thorax.

Semi-solid S701: S701/SUP A/BUP (79/13/8)

Semi-solid S701+BetV: S701/SUP A/BUP (78.95/13/8/0.05)

Gel DM: CO/SUP DM/BUP (81/11/8)

Gel DM+BetV: CO/SUP DM/BUP/BETV (80.95/11/8/0.05)

Injection site reaction of edema/erythema data were evaluated according Table 13.

TABLE 13

Evaluation of Skin Reactions

| Erythema and Eschar Formation | Score |
|---|---|
| No erythema | 0 |
| Very slight erythema (barely perceptible) | 1 |
| Well-defined erythema | 2 |
| Moderate to severe erythema | 3 |
| Severe erythema (beet redness) to slight eschar formation (injuries in depth) | 4 |

| Edema Formation | Score |
|---|---|
| No edema | 0 |
| Very slight edema (barely perceptible) | 1 |
| Slight edema (edges of area well-defined by definite raising) | 2 |
| Moderate edema (raised approximately 1 mm) | 3 |
| Severe edema (raised more than 1 mm and extending beyond area of exposure) | 4 |

Injection site edema/erythema results for the tested formulations is shown in Tables 14 and 15. Palpable masses (edema score of 2 to 3), attributed to depositing of the semi-solid formulations, were evident at the dosing area in all animals right after injection. Semi-solid S701 exhibited edema at Day 1 and Day 2, and gradually subsided from Day 3 to Day 8. In the presence of 0.05% betamethasone valerate, edema was eliminated. Semi-solid S701 also exhibited moderate erythema at Day 1 and Day 2, and gradually subsided from Day 3 to Day 8. In the presence of 0.05% betamethasone valerate, erythema was reduced at Day 1 and Day 2.

The bupivacaine castor oil gel formulation, Gel DM, only exhibited very slight or minimal edema and erythema at the injection sites.

TABLE 14

Skin reaction (Edema) results after 0.5 mL subcutaneous injection

| Semi-solid gel Formulation ID | Day 1 | Day 2 | Day 3 | Day 4 | Day 5 | Day 6 | Day 7 | Day 8 |
|---|---|---|---|---|---|---|---|---|
| S701 | 4.0 | 4.0 | 3.3 | 2.3 | 2.0 | 2.0 | 1.3 | 1.3 |
| S701 + BETV | 2.0 | 1.7 | 1.7 | 1.0 | 1.0 | 1.0 | 1.0 | 0.7 |
| Gel DM | 3.0 | 2.5 | 2.5 | 2.5 | 2.0 | 2.0 | 1.5 | 1.5 |
| CO DM + BETV | 2.5 | 2.0 | 2.0 | 1.5 | 1.5 | 1.5 | 1.0 | 1.0 |

TABLE 15

Skin reaction (Erythema) results after 0.5 mL subcutaneous injection

| Semi-solid Formulation ID | Day 1 | Day 2 | Day 3 | Day 4 | Day 5 | Day 6 | Day 7 | Day 8 |
|---|---|---|---|---|---|---|---|---|
| S701 | 3.0 | 3.0 | 2.0 | 1.7 | 1.7 | 1.0 | 0.7 | 0.7 |
| S701 + BETV | 1.7 | 1.3 | 1.0 | 1.0 | 0.7 | 0.3 | 0.3 | 0.3 |

Example 15. In Vivo Rat Sciatic Nerve Blockade Tests

Male rats weighing between 200 g and 250 g were used to assess the duration of nerve conduction block, which induced by each of the different semi-solid formulations had been tested. The rats were handled daily and habituated to the testing paradigm for at least 60 minute prior to examination. Sensory and motor blockade were examined as described below. In addition to sensory testing, motor testing was performed at each time point to examine the ability of the rats to move their hind leg by gait posture and paw placing. Animals were handled and cared in compliance with institutional, state, and federal animal welfare regulation. The protocol was approved by IACAC.

All rats were anesthetized with 3.5% to 4.0% isoflurane in oxygen and maintained with 1.5%-2.0% isoflurane. Under aseptic condition, the left thigh area was shaved and an incision was made on the upper ⅓ portion. The thigh muscles were gently dissected by blunt dissection to expose the sciatic nerve. Semi-solid gel formulations were placed adjacent to the sciatic nerve under direct vision in the fascia plane deep to the hamstrings and the site. The most superficial fascia layer was closed with a single suture. The edges of the outer skin were approximated and closed with surgical staples. For all rats, drug-containing semi-solid formulations were implanted on the left side of sciatic nerve.

Hot-plate measurement: for each time-point, the rat was put on 56° C. hot-plate and the latency of lifting the hind paw was recorded (for both paws of the animal) for three times with intervals at least 5 minutes. A cutoff latency of 10 seconds was used to prevent development of hyperalgesia or injury. The average of three readings was used as the final reading for the particular time-point.

Paw placing: for both paws, the animals were held gently by a trained researcher and the dorsal paw, one at a time, was slowly slid over a edge of test platform until the toes were reached and repeated 5 times. At each time, if the rat successfully places its testing paw onto the surface of the platform, it was scored as 1 (therefore, the maximum score is 5 for each paw) and as 0 if it fails.

Paw motor ability measurement: The paw motor ability test, utilizing a scale of 1 to 4, evaluates the animal's ability to hop and place weight on its hind leg, according to following levels (Castillo, 1996, Anesthesiology 85:1157-66):

(1) normal appearance.
(2) intact dorsiflexion, but impaired splaying toes when elevating the tail of rat.
(3) completely plantar flexion without splaying ability.
(4) number 3 plus impaired gait.

The paw motor ability assessment was used for each time-point as well. For both paws, the animals were held gently by a trained researcher dorsally.

Dissection: At two week time points following the administration, and the surgical site skin was examined to observe if any affection on wound healing. Then after, the sites where the semi-solid formulation was administered were re-opened and examined visually by naked eyes under anesthesia. After the examination was finished, the rats were euthanized by $CO_2$.

1. Desired Efficacy/Analgesia Profile for Post-surgical Pain Relief

The first day immediately following surgery is extremely painful and demands robust analgesia coverage to ensure pain relief and opioid abstinence. If products do not provide sufficient analgesia for the first day, rescue opioid medication is needed.

Ideally, the bupivacaine semi-solid gel formulations provide (1) a fast enough release to provide the desired analgesic coverage through the first crucial 24 hours post traumatic injury, (2) a slow enough release to sufficiently prolong the duration of effect through 72 hour, (3) a dose adequate for release at the required rate over the prolonged period of time and (4) a volume small enough and viscosity low enough for convenient administration, which has been very difficult to achieve.

2. Bupivacaine Castor Oil Gel Formulation

Figure 5:
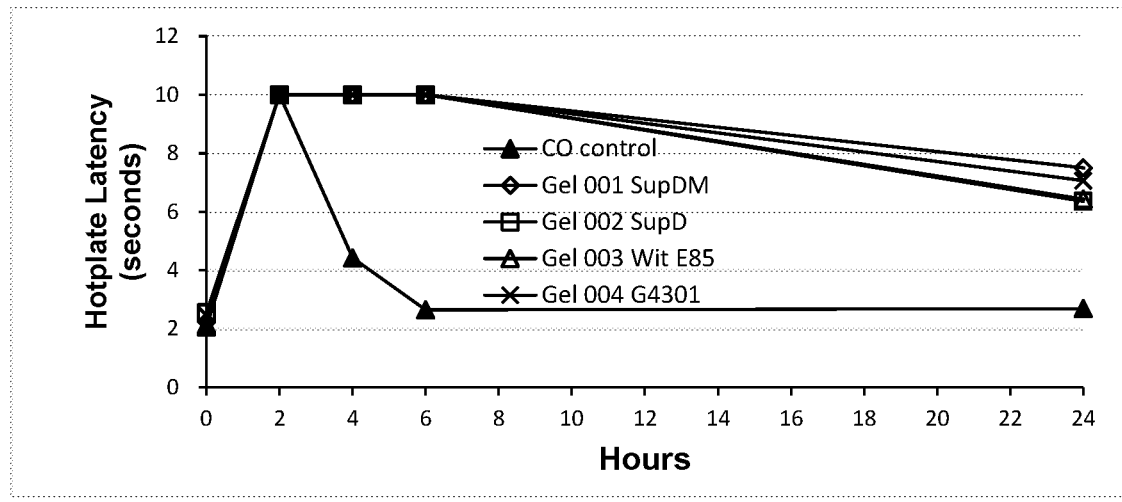
FIGS. 5 and 5a show hotplate latencies versus time as a measure of sensory function for a series of bupivacaine castor oil gel formulations, including.
Figure 5A:
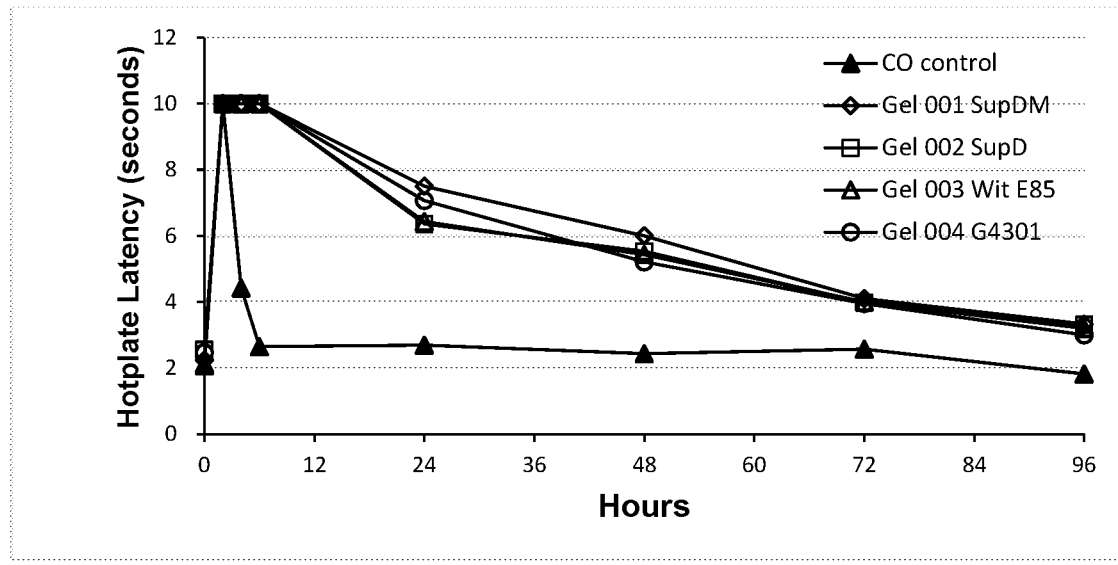

The pharmacodynamic activity of bupivacaine released from castor oil gel formulation yielded greater analgesic activity compared to bupivacaine in castor oil alone when evaluated in the rat sciatic nerve blockade model (FIG. 5).

Hotplate latencies versus time as a measure of sensory function for bupivacaine castor oil gel formulations are shown in FIG. 5. Sensory blockade was evaluated using left hind paw latency response time recording on a 56° C. hotplate.

A bupivacaine castor oil solution formulation containing 8 wt % bupivacaine was used as a control formulation. Castor oil bupivacaine oil solution yielded a limited analgesic response of approximately 4-6 hours in the rat sciatic nerve blockade model, thanks to its relatively high viscosity and relatively slow dissolution of bupivacaine free base into body fluid.

However, with the help of gelling agents, castor oil bupivacaine gel formulations provides robust sensory and motor blockade over the first 24 hours, and extended partial blockade up to 72 hours commensurate with the degree of analgesia (moderate block for the second day, partial block for the third day, which underscores the pain intensity profile of typical surgical patients with extreme pain for the first day, moderate pain for the second day, and only minor pain for the third day.)

Paw motor ability measurement versus time for bupivacaine castor oil gel formulations were presented in FIG. 6. The paw motor ability test, utilizing the scale of 1 to 4, evaluates the animal's ability to hop and place weight on its hind leg.

The bupivacaine castor oil gel formulations groups yielded dense motor blockade over the first 24 hours and extended partial blockade up to 48 hours commensurate with the degree of analgesia (FIG. 6), while the bupivacaine castor oil solution formulation yielded dense motor blockade for 2 hours and extended partial blockade up to 6 hours. Dense motor blockade for the first 24 hours post traumatic surgery is necessary to offer effective analgesia. Motor function was reversible in all groups, which had returned to normal values 72 hours post administration.

Surgical Site Wound Healing and Dissection:

At two week time points following the administration, the surgical site skin was examined to observe if any effect on wound healing. No adverse effect of the gel formulations on wound healing was observed, and the surgical sites healed well in approximately two weeks. Only slight edema and erythema was observed for bupivacaine castor oil gel formulations after formulation administration.

The sites where the gel formulation was administered were re-opened and examined visually by naked eyes under anesthesia. The administration site appeared to be pinkish, and the sciatic nerve appeared to be normal, no inflammation, necrosis, ulceration, or infection was observed. In addition, most of the gel formulation was dissolved and absorbed, and only a small amount of depot residue was observed at the administration site.

3. Bupivacaine Castor Oil Gel Formulation with an Anti-inflammatory

The inflammatory response after an acute injury, as with a surgical incision, results in postoperative inflammation which impairs the ability of local anesthetics, including bupivacaine, to block sensory nerve conduction. The latter is as a result of the acidic environment generated by the inflammatory response impeding the analgesic from penetrating the nerve cell membrane. Bupivacaine castor oil gel formulations with an anti-inflammatory were created to overcome the surgical inflammatory response by incorporating an anti-inflammatory such as BET, BETV, MP, KETO, or TA, to maximize pain reduction through 72 hours.

Bupivacaine castor oil gel formulations with an anti-inflammatory enhanced nerve blockade, compared to bupivacaine castor oil gel formulations without an anti-inflammatory, was observed through 72 hours.

As confirmed with the addition of the anti-inflammatory, bupivacaine castor oil gel formulations afforded greater analgesic effect (increased strength) over the first 24 hours with both dense sensory and motor blockade and moderate partial blockade through 72 hours post traumatic injury compared to bupivacaine castor oil gel formulations without an anti-inflammatory. In addition, bupivacaine castor oil gel formulations with anti-inflammatory even extend partial sensory blockade through 96 hours and up to 120 hours. (FIGS. 7 and 8.) Therefore, bupivacaine castor oil gel formulations with anti-inflammatory can be used for the management of post-operative pain for a wide range of different types of very painful surgeries such as moderate/major abdominal, gynecological, thoracic, and orthopedic surgeries etc. to expand clinical utility.

Stability of Bupivacaine CO Semi-solid Gel Formulations

Bupivacaine CO gel formulations are stable to heat treatment and terminal sterilization by autoclaving and under various storage conditions of at −5° C., 4° C., 25° C., and 40° C. They were prepared and filled into glass pre-filled syringes and the resulted formulations was sterilized using autoclave (steam sterilization cycle 121° C.×20 minutes). The total bupivacaine related substance was approximately 0.10% after manufacturing and the steam sterilization cycle. After being stored at 40° C. for one month, an additional 0.1% bupivacaine was degraded/oxidized. Bupivacaine CO gel formulations are expected to be stable under room temperature conditions. In addition, no phase separation or precipitation or drug crystallization during all the above storage conditions for one month.

What is claimed:

1. A pharmaceutical formulation, comprising
    (A) a glyceride mixture comprising
        (i) triglyceride of ricinoleic acid; and
        (ii) glycerides selected from the group consisting of (a) a mixture of $C_{12}$ to $C_{18}$ triglycerides (SUP DM) (b) a mixture of $C_8$ to $C_{18}$ triglycerides (G43/01); (c) a mixtures of hydrogenated coco-glycerides (WIT E85 and WIT E76); and (d) a mixture of $C_{10}$ to $C_{18}$ triglycerides (SUP D); or other solid glycerides with a melting point between 37° C. and 75° C.;
    wherein the ratio (i):(ii), is 10:1 to 6:3 (w:w); and
    (B) a therapeutically effective amount of bupivacaine to provide analgesia for at least two days; and, optionally, an active ingredient selected from a corticosteroid, an analgesic and an anti-inflammatory agent, wherein total concentration of bupivacaine and the optional active ingredient is 0.01-60 wt % in the glyceride mixture;
    wherein the pharmaceutical composition is a semi-solid gel which is biocompatible, bioerodible, homogeneous, and a single phase; wherein the semi-solid gel has a viscosity of 50-2000 cPs at 30° C., and wherein less than 80% of the bupivacaine is released from a depot of the semi-solid gel in five days when measured in vitro at 37° C.

2. The pharmaceutical formulation of claim 1, comprising bupivacaine and the active agents selected from a corticosteroid, an analgesic and an anti-inflammatory agent.

3. The pharmaceutical formulation of claim 2, wherein the corticosteroid is a glucocorticosteroid.

4. The pharmaceutical formulation of claim 2, wherein the anti-inflammatory agent is a non-steroidal anti-inflammatory agent (NSAID) selected from the group consisting of ketoprofen, naproxen, meloxicam, COX-1 inhibitors, and COX-2 inhibitors.

5. The pharmaceutical formulation of claim 1, wherein the glyceride mixture comprises SUP DM.

6. The pharmaceutical formulation of claim 1, wherein the triglyceride of ricinoleic acid is castor oil and wherein glyceride mixture comprises castor oil:SUP DM having a relative concentration of 8:1.0, 8:1.1, 8:1.2, 8:1.3, 8:1.4, 8:1.5, 8:1.6, 8:1.7, 8:1.8, 8:1.9, 8:2.0, 8:2.1, 8:2.2, 8:2.3, 8:2.4:, or 8:2.5 (w:w).

7. The pharmaceutical formulation of claim 1, wherein less than 60% of the bupivacaine is released from a depot of the semi-solid gel in five days when measured in vitro at 37° C.

8. The pharmaceutical formulation of claim 1, wherein less than 66% of the bupivacaine is released from a depot of the semi-solid gel in five days when measured in vitro at 37° C.

9. The pharmaceutical formulation of claim 1, wherein the viscosity is less than 701 cPs at 30° C.

10. The pharmaceutical formulation of claim 1, wherein the pharmaceutical composition releases bupivacaine for at least one week when measured in vitro at 37° C.

11. The pharmaceutical formulation of claim 1, wherein the pharmaceutical composition releases bupivacaine for at least two weeks when measured in vitro at 37° C.

12. The pharmaceutical formulation of claim 1, wherein glyceride mixture has an aqueous solubility of less than 1 mg/ml or less than 0.1 mg/ml in a buffer of physiological pH at 37° C.

13. The pharmaceutical formulation of claim 1, wherein the glyceride mixture comprises castor oil.

14. The pharmaceutical formulation of claim 1, wherein the glyceride mixture comprises ricinoleic acid triester: SUP DM, having a relative concentration of 8:1.8 (w:w).

15. The pharmaceutical formulation of claim 13, wherein the viscosity is less than 701 cPs at 30° C.

16. The pharmaceutical formulation of claim 13, wherein the pharmaceutical composition releases bupivacaine for at least one week when measured in vitro at 37° C.

17. The pharmaceutical formulation of claim 13, wherein the pharmaceutical composition releases bupivacaine for at least two weeks when measured in vitro at 37° C.

18. The pharmaceutical formulation of claim 1, for use in treating pain following surgery.

19. The pharmaceutical formulation of claim 1, wherein a single injection of the pharmaceutical formulation comprises an amount of bupivacaine effective to provide sensory blockade for 72 hours.

20. The pharmaceutical formulation of claim 1, wherein a single injection of the pharmaceutical formulation causes substantially limited motor blockade.

* * * * *